United States Patent [19]
Atkinson et al.

[11] Patent Number: 6,028,310
[45] Date of Patent: *Feb. 22, 2000

[54] LINEAR CAVITY LASER SYSTEM FOR INTRACAVITY LASER SPECTROSCOPY

[75] Inventors: George H. Atkinson; Esmail Mehdizadeh; Jeffrey S. Pilgrim, all of Tucson, Ariz.

[73] Assignee: Innovative Lasers Corporation, Tucson, Ariz.

[*] Notice: This patent is subject to a terminal disclaimer.

[21] Appl. No.: 08/971,861

[22] Filed: Nov. 17, 1997

Related U.S. Application Data

[63] Continuation-in-part of application No. 08/675,531, Jul. 3, 1996, Pat. No. 5,723,864, which is a continuation-in-part of application No. 08/675,605, Jul. 3, 1996, Pat. No. 5,747,807, which is a continuation-in-part of application No. 08/522,963, Sep. 1, 1995, Pat. No. 5,689,334.

[51] Int. Cl.$^7$ ............................................. G01N 21/35
[52] U.S. Cl. .................. 250/339.13; 250/343; 356/328; 372/41
[58] Field of Search ............... 250/339.13, 337.12, 250/343; 356/326, 328, 300, 436, 437, 438, 439; 372/41, 66, 70

[56] References Cited

U.S. PATENT DOCUMENTS

| | | | |
|---|---|---|---|
| 4,464,761 | 8/1984 | Alfano et al. | 372/41 |
| 4,648,714 | 3/1987 | Benner et al. | 356/301 |
| 5,432,610 | 7/1995 | King et al. | 356/432 |
| 5,459,745 | 10/1995 | Esterowtiz et al. | 372/41 |
| 5,723,864 | 3/1998 | Atkinson et al. | 250/339.13 |

OTHER PUBLICATIONS

Stephen R. Chinn, et al, "Spiking Oscillations in Diode–Pumped $NdP_5O_{14}$ and $NdAl_3(BO_3)_4$ Lasers", IEEE Journal of Quantum Electronics, vol. QE–12, No. 3 Mar. pp. 189–193 (1976).

G. Atkinson et al, "Detection of Free Radicals by an Intracavity Dye Laser Technique", vol. 59, No. 1, Journal of Chemical Physics, Jul. 1, 1973, pp. 350–354.

D. Gilmore et al, "Intracavity Absorption Spectroscopy With A Titanium: Sapphire Laser", Optics Communications, vol. 77, No. 5.6, pp. 385–389 Jul. 15 (1990).

G. Atkinson, "Intracavity Laser Spectroscopy", SPIE Conference, Soc. Opt. Eng. 1637 (1992) 126–133.

D. Gilmore et al, "Intracavity Laser Spectroscopy in the 1.38–1.55 ηm Spectral region Using a Multimode $Cr^{4+}$: YAG Laser, " Optics Communications 103 pp. 370–374 (1993).

A. Kachanov et al, "Intracavity Laser Spectroscopy With Vibronic Solid State Lasers: I. Spectrotemporal Transient Behavior Of A TI: sapphire Laser", Journal of the Optical Society of America B, 11 pp. 2412–2421 (1994).

Primary Examiner—Constantine Hannaher
Assistant Examiner—Albert Gagliardi
Attorney, Agent, or Firm—Benman & Collins

[57] ABSTRACT

Contaminants are detected optically at concentrations below 100 part-per-million (ppm) and extending to a level approaching 1 part-per-trillion (ppt) by using intracavity laser spectroscopy (ILS) techniques. An optically-pumped solid-state laser (the ILS laser) is employed as a detector. The ILS laser comprises an ion-doped crystal medium contained in a linear laser cavity. A gas sample containing gaseous contaminant species is placed inside the laser cavity and on one side of the ion-doped crystal. The output signal from the ILS laser is detected and analyzed to identify the gaseous species (via its spectral signature). The concentration of the gaseous species can be determined from the spectral signature as well. One preferred embodiment of the present invention employs a linear cavity formed between two mirrors separated from the ion-doped crystal laser medium, wherein both ends of the ion-doped crystal are cut at Brewster's angle.

41 Claims, 11 Drawing Sheets

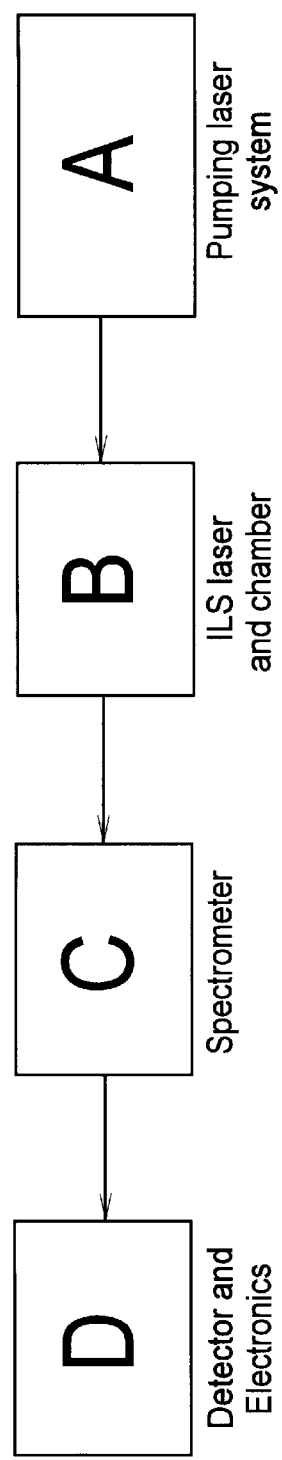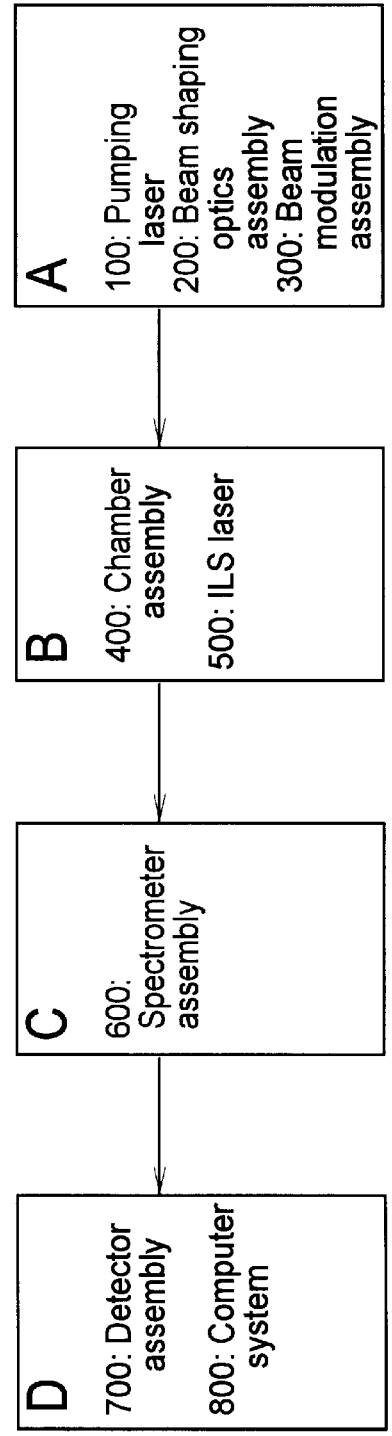
FIG. 1A
FIG. 1B

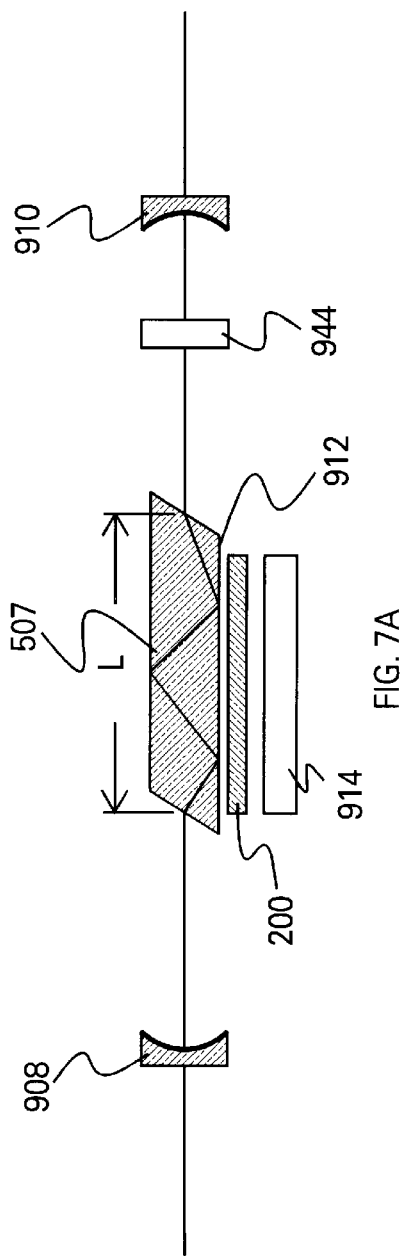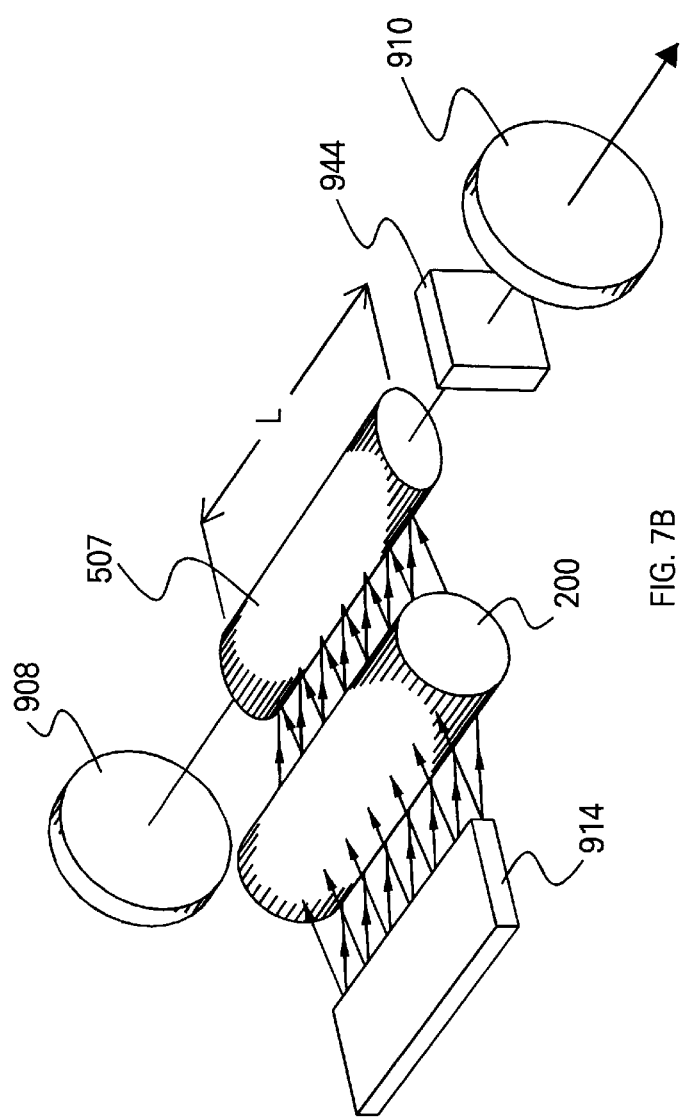
FIG. 7A
FIG. 7B

LINEAR CAVITY LASER SYSTEM FOR INTRACAVITY LASER SPECTROSCOPY

CROSS-REFERENCE TO RELATED APPLICATION

This application is a continuation-in-part application of application Ser. No. 08/675,531 filed on Jul. 3, 1996, now U.S. Pat. No. 5,723,864, issued Mar. 3, 1998, which in turn is a continuation-in-part application of application Ser. No. 08/675,605, filed on even date herewith, now U.S. Pat. No. 5,747,807, issued Apr. 21, 1998 which in turn is a continuation-in-part application of application Ser. No. 08/522,963, filed on Sep. 1, 1995, now U.S. Pat. No. 5,689,334, issued Nov. 18, 1997.

This application is related to the continuation-in-part application Ser. No. 08/971,862, filed on even date herewith, now U.S. Pat. No. 5,917,188 issued Jun. 29, 1999. That application concerns an ILS laser pumped with a semiconductor diode laser. The present application is directed to an ILS laser having a laser cavity that is a linear cavity.

TECHNICAL FIELD

This invention relates, generally, to the detection of contaminants in gases, and more particularly, to the high sensitivity detection of gaseous molecules, atoms, radicals, and/or ions by laser techniques generally termed intracavity laser spectroscopy (ILS).

BACKGROUND OF THE INVENTION

In the preparation of high quality semiconductor material (e.g., silicon films) for use in the microelectronics industry, it is well known that contaminants must be controlled. Failure to control contaminants, as is also well known and appreciated, can result in the loss of significant resources as the resultant products are typically not useful for their intended purposes.

Generally, the starting materials in the fabrication of silicon films consist essentially of gases, typically denoted either "bulk" (e.g., nitrogen or argon) or "specialty" (e.g., hydrogen chloride, hydrogen bromide, boron trichloride). The successful operation of a fabrication facility designed to prepare semiconductor materials depends directly on the purity of the starting gases, as well as the gas handling capabilities available to preserve gas purity during the delivery of the gases to the process chamber and while material processing is taking place. Suitable control of the purity of such starting gases (i.e., monitoring and inhibiting high levels of contaminants as may be contained in the gases) is essential.

Under many current techniques, such control is achieved after the fact. That is, the silicon films so produced are periodically tested and the production line shut down only after such tests reveal the presence of high level contaminants. These processes, as will be appreciated by those skilled in the art, can lead to the waste of not only starting materials but also product which is produced prior to cessation of production. It is therefore desirable to monitor and control the contaminants as may be contained in such starting gases during production so as unacceptable contaminant levels are observed, production can be immediately, or at least shortly thereafter, halted.

Many molecular, atomic, radical, and ionic species are present in the bulk and specialty gases used in the preparation (e.g., chemical vapor deposition or "CVD") and processing (doping and etching) of semiconductor materials that can be viewed as "contaminants." Such contaminants can degrade either the quality of the fabricated semiconductor material or the efficiency with which the semiconductor material is prepared. These contaminant species can interfere with the chemical process directly or even cause particles to be formed in the gas delivery lines or process chamber, which subsequently deposit on the surface of the wafer material causing indirect performance defects.

The first step in controlling and/or eliminating these contaminants is their detection in the bulk and specialty gases used as starting materials. While this is generally recognized, heretofore practiced methods are generally inadequate. This is due, in large part, to the situation created by seemingly ever increasing competitive industry standards which have developed. Specifically, as the size of microelectronic devices has decreased while performance specifications have been intensified, the requirements for gas purity (i.e., absence of microcontamination) has increased.

Against this backdrop, it will likely be clear that several measurement criteria are important to detector effectiveness: (1) absolute detection sensitivity usually stated as parts-per-total number of gas molecules in the sample (e.g., parts-per-million or number of contaminant molecules per $10^{+6}$ background molecules); (2) species selectivity or the capability to measure the concentration of one species in the presence of other species; (3) rapidity of measurements to obtain a desired signal to noise ratio; (4) capability of monitoring contaminants in both non-reactive and reactive gases; and (5) linearity and dynamic range of gas concentrations that can be measured.

The current state-of-the-art devices for contaminant detection (e.g., water) encompass a variety of measurement techniques. For example, current state-of-the-art devices for water vapor detection utilize conductivity and electrochemical, direct absorption spectroscopy, and atmospheric pressure ionization mass spectroscopy (APIMS) measurement techniques. As discussed below, each of these methods fails to adequately address these requirements.

Conductivity and Electrochemical

Conductivity and electrochemical methods by solid-state devices exist which can detect water vapor at the 1 to 100 ppm range. Conductivity and electrochemical methods generally require direct physical contact between the sample and the device; thus, detection occurs after water molecules deposit on the solid-state surface. As a consequence, these devices do not perform well, if at all, with utilization of reactive or corrosive gases. Indeed, even their performance in non-reactive gases changes and/or deteriorates after even short exposures to reactive or corrosive gases. The linearity and dynamic range of response are usually limited to about one decade. The detection selectivity of these devices with respect to different gaseous species also is generally poor since the devices themselves will respond to a wide range of species without discrimination. Additionally, selectivity is incorporated into the measurements only through whatever chemical selectivity, if any, is embodied in the coatings used to cover these devices.

Direct Absorption

Direct absorption spectroscopy generally relates to the passing of light through the sample from an external source and measuring the reduction in light intensity caused by molecular, atomic, radical, and/or ionic absorption in the sample. Detection sensitivity depends directly on the subtraction of two large numbers (light intensity from the external source before it passes through the sample and its intensity after it exits the sample). This limits the detection sensitivity to the extent that direct absorption is generally considered a low sensitivity methodology.

APIMS

APIMS, initially used in the analysis of impurities in bulk nitrogen and argon and ambient air for air pollution studies, is now currently used by semiconductor manufacturers to detect trace levels of moisture and oxygen in inert bulk gases. With APIMS, the sampled gas is bombarded with electrons, or may be flame and photon excited, to produce a variety of ions that are then detected directly. Particularly, ionization occurs at atmospheric pressure in the presence of a reagent gas in the ionization source. APIMS typically exhibits detection sensitivities in the range of about 10 parts per trillion (ppt) in non-reactive gases. APIMS cannot even be used with reactive gas mixtures. Additional disadvantages of APIMS include an average cost between about $150,000 to $250,000, extensive purging and calibration procedures, and the need for a knowledgeable operator.

Intracavity Laser Spectroscopy

In the context of the present invention, laser technology, specifically intracavity laser spectroscopy (ILS), is disclosed as being used as a detector (sensor) to detect gaseous species (contaminants) at very high sensitivity levels. While the methods and apparatus disclosed herein are particularly suited for application in fabrication of semiconductor components, it should be appreciated that the present invention in its broadest form is not so limited. Nevertheless, for convenience of reference and description of preferred exemplary embodiments, this application will be used as a benchmark. In connection with this application, laser technology offers distinct advantages to gaseous species (contaminant) detection over known methods and, particularly, to water vapor detection.

In conventional applications of lasers to the detection of gaseous species (contaminants), laser produced radiation is used to excite the gas sample external to the laser in order to produce a secondary signal (e.g., ionization or fluorescence). Alternatively, the intensity of the laser after it passes through a gas sample, normalized to its initial intensity, can be measured (i.e., absorption).

Some twenty years ago, another detection methodology, intracavity laser spectroscopy, was first explored in which the laser itself is used as a detector; see, e.g., G. Atkinson, A. Laufer, M. Kurylo, "Detection of Free Radicals by an Intracavity Dye Laser Technique," 59 *Journal Of Chemical Physics*, Jul. 1, 1973.

Intracavity laser spectroscopy (ILS) combines the advantages of conventional absorption spectroscopy with the high detection sensitivity normally associated with other laser techniques such as laser-induced fluorescence (LIF) and multiphoton ionization (MPI) spectroscopy. ILS is based on the intracavity losses associated with absorption in gaseous species (e.g., atoms, molecules, radicals, or ions) found within the optical resonator cavity of a multimode, homogeneously broadened laser. These intracavity absorption losses compete via the normal mode dynamics of a multimode laser with the gain generated in the laser medium. Traditionally, ILS research has been dominated by the use of dye lasers because their multimode properties fulfill the conditions required for effective mode competition and their wide tunability provides spectral access to many different gaseous species. In particular, measurements at visible wavelengths have been conducted using dye lasers having linear two-mirror cavities; see, e.g., V. M. Baev, J. Eschner, J. Sierks, A. Weiler, and P. E. Toschek, "Regular dynamics of a multimode dye laser", *Optics Communications*, 94 (1992) 436–444; and J. Sierks, V. M. Baev, and P. E. Toschek, "Enhancement of the sensitivity of a multi-mode dye laser to intracavity absorption", *Optics Communications*, 96 (1993) 81–86.

The liquid dye laser, however, is not compatible with many practical applications given its liquid state and the need to maintain physical and optical stability. Dye lasers also operate primarily in the visible spectral region. The absorption strength of any gaseous species, although definitely detectable by ILS, are not as strong in the visible as compared to lower energies (e.g., in the near infrared). Higher detection sensitivity, therefore, is found when absorption transitions in the infrared are utilized.

Some ILS experiments have been performed with multimode, tunable solid-state laser media such as color centers and Ti:Sapphire; see, e.g., D. Gilmore, P. Cvijin, G. Atkinson, "Intracavity Absorption Spectroscopy With a Titanium: Sapphire Laser," *Optics Communications* 77 (1990) 385–89.

ILS has also been successfully used to detect both stable and transient species under experimental conditions where the need for high detection sensitivity had previously excluded absorption spectroscopy as a method of choice. For example, ILS has been utilized to examine gaseous samples in environments such as cryogenically cooled chambers, plasma discharges, photolytic and pyrolytic decompositions, and supersonic jet expansions. ILS has been further used to obtain quantitative absorption information (e.g., line strengths and collisional broadening coefficients) through the analysis of absorption lineshapes. Some of these are described in G. Atkinson, "Intracavity Laser Spectroscopy," SPIE Conf., *Soc. Opt. Eng.* 1637 (1992).

Prior art methods of performing ILS, however, while suitable for use in laboratory settings are unacceptable for commercial settings. The constraints of commercial reality, as briefly noted above, essentially dictate that such a detector be conveniently sized, relatively inexpensive, and reliable. Laboratory models fail to fully meet these requirements.

A laboratory demonstration of the feasibility of using ILS techniques for detecting small quantities of water vapor in a nitrogen atmosphere with a $Cr^{4+}$:YAG laser is described in D. Gilmore, P. Cvijin, G. Atkinson, "Intracavity Laser Spectroscopy in the 1.38–1.55 $\mu$m Spectral Region Using a Multimode $Cr^{4+}$:YAG Laser," *Optics Communications* 103 (1993) 370–74. The experimental apparatus utilized was satisfactory for demonstration of operational characteristics, but undesirable for implementation in a commercial application as contemplated by the present invention.

In accordance with various aspects of the present invention, the present invention provides a user friendly, i.e., comparatively simple, detection system, having the advantages of direct absorption techniques but with dramatically increased detection sensitivities, capable of detecting gaseous species in reactive and non-reactive samples at a commercially viable cost. In this regard, the present invention addresses the long felt need for a method and apparatus for the high sensitivity detection of contaminants in reactive and non-reactive gas systems in commercial settings.

SUMMARY OF THE INVENTION

In accordance with various aspects of the present invention, contaminants are detected optically at concentrations below 100 part-per-million (ppm) and extending to a level approaching 1 part-per-trillion (ppt) by using ILS techniques. An optically pumped solid-state laser comprising an optical resonator cavity that is a linear cavity formed between two mirrors with an ion-doped crystal medium contained therein, serves as the detector. A gas sample containing gaseous contaminant species, for example, water vapor, is placed inside the linear cavity of the ion-doped laser (between the two mirrors or reflective surfaces) and on one side of the active medium. A variety of ion-doped laser media including $Tm^{3+},Tb^{3+}$:YLF and $Tm^{3+}$:YAG are described here, but other ion-doped crystals having multiple longitudinal and transverse cavity modes can be used as well. An optical pumping source such as a laser (e.g., a semiconductor diode laser) is used to pump the solid-state laser, and beam shaping optics are employed to focus the output of the pumping source on the ion-doped crystal medium.

Specifically, a gas detection system for detecting the presence of gaseous species in a gas sample is provided. The gas detection system comprises:

(a) a linear laser cavity formed between a first mirror and a second mirror;

(b) an ion-doped crystal therein having two ends;

(c) a pumping source located outside the linear laser cavity, which has an output that optically excites the ion-doped crystal, thereby producing an output beam that exits the linear laser cavity;

(d) beam shaping optics located outside the linear laser cavity that shapes the output of the pumping source, wherein the beam shaping optics are selected from the group consisting of diffractive optics, refractive optics, fiber optics, gradient index optics wherein the refractive index varies axially, gradient index optics wherein the refractive index varies radially, micro-optics, and combinations thereof;

(e) a container for containing the gas sample in the linear laser cavity, the output beam of the ion-doped crystal passing through the gas sample prior to exiting the linear laser cavity;

(f) a spectrometer wherein the output beam of the ion-doped crystal after exiting the linear laser cavity is directed to the spectrometer; and (g) a detector assembly including therein a detector, wherein the output beam of the ion-doped crystal after exiting the spectrometer is directed to the detector assembly for determining the presence and/or concentration of gaseous species in the gas sample.

The gas detection system preferably comprises a pump source such as a semiconductor laser diode, an ion-doped crystal laser (e.g., $Cr^{4+}$:YAG), a gas laser, flashlamps, or other suitable forms of optical pumping used to provide the optical excitement required to operate the ILS laser, a multimode ILS laser operated over the wavelength region in which the species of interest absorb, beam steering optics, a gas sample placed within the linear laser cavity of the ILS laser (either by employing a gas sample cell located within the linear laser cavity or by filling the entire intracavity optical region with the gas sample), a wavelength dispersive spectrometer capable of spectrally resolving the output of the ILS laser, and an electronic circuit which can read the signal from the detector and convert it into an electronic signal that can be processed by a computer or other digital electronics. The gas detection system may also include a modulating device designed to periodically interrupt the intensity of the pumping laser beam and the output from the ILS laser. One specific embodiment of the present invention comprises a linear cavity formed between two mirrors separated from the ion-doped crystal gain medium, wherein both ends of the ion-doped crystal are cut at an appropriate Brewster's angle.

A method for detecting the presence of gaseous species in a gas sample is also disclosed. The method comprises the steps of:

(a) providing a linear laser cavity formed between a first mirror and a second mirror having an ion-doped crystal contained therein;

(b) providing a pumping source situated so that the output beam of the pumping source is directed to the ion-doped crystal to pump the crystal to produce an output beam from the ion-doped crystal;

(c) providing a container for containing the gas sample within the linear laser cavity so that the output beam from the ion-doped crystal passes through the gas sample prior to exiting the linear laser cavity;

(d) providing beam shaping optics outside the linear laser cavity that shape the output of the pumping source, the beam shaping optics being selected from the group consisting of diffractive optics, refractive optics, fiber optics, gradient index optics wherein the refractive index varies axially, gradient index optics wherein the refractive index varies radially, micro-optics, and combinations thereof;

(e) providing a spectrometer situated so that the output beam from the ion-doped crystal after exiting the linear laser cavity is directed to the spectrometer; and (f) providing a detector assembly situated so that the output beam from the ion-doped crystal after exiting the spectrometer is directed to the detector assembly for determining the presence and/or concentration of gaseous species in the gas sample.

BRIEF DESCRIPTION OF THE DRAWINGS

Preferred exemplary embodiments of the present invention will be hereinafter described in conjunction with the appended drawing figures, wherein like designations denote like elements. The drawings referred to in this description should be understood as not being drawn to scale except if specifically noted.

FIGS. 1A and 1B are schematic block diagrams of a contaminant detector system in accordance with the present invention; FIG. 1A shows the basic configuration, while FIG. 1B shows that configuration as embodied in one embodiment shown in FIGS. 3 and 4;

FIGS. 7A and 7B are schematic and perspective representations, respectively, of an additional configuration of the ILS laser of the present invention wherein transverse pumping is employed to pump the ion-doped crystal gain medium;

DESCRIPTION OF THE PREFERRED EMBODIMENTS

Figure 2A:
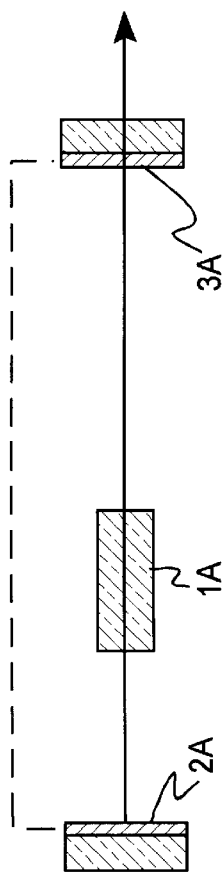
FIGS. 2A–2C includes schematic representations of simple laser devices.

Reference is now made in detail to a specific embodiment of the present invention, which illustrates the best mode presently contemplated by the inventors for practicing the invention. Alternative embodiments are also briefly described as applicable.

As previously briefly noted, the subject matter of the present invention is particularly well suited for use in connection with the manufacture of semiconductor components, and thus, a preferred exemplary embodiment of the present invention will be described in that context. It should be recognized, however, that such description is not intended as a limitation on the use or applicability of the subject invention, but rather is set forth to merely fully describe a preferred exemplary embodiment thereof.

In this regard, the present invention is particularly suited for detection of contaminants. Contaminants as used herein refer to molecular, atomic, radical, and ionic species such as may be present in gaseous materials, such as in the gaseous materials which are used in the fabrication of silicon films, i.e., inlet lines. Alternatively, the term contaminant may also refer to the gaseous material itself, such as, for example, when the detector of the present invention is used to determine if a line (e.g., HCl line) has been sufficiently purged of the gaseous material.

In accordance with one embodiment of the present invention and with momentary reference to FIG. 1A, a gas (contaminant) detector system 10 suitably comprises a pumping laser system A, an ILS laser and associated chamber B, a spectrometer C, and a detector with associated electronics (e.g., computer, digital electronics, etc.) D. More particularly, and with reference to FIGS. 1B and 4, pumping system A suitably comprises a pumping source 100, a beam shaping optics assembly 200 and a beam modulation assembly 300; laser and chamber B suitably comprises a chamber assembly 400 and an ILS laser 500; spectrometer C suitably comprises a spectrometer assembly 600; and detector D suitably comprises a detector assembly 700 and a computer system 800. As will be described more fully herein, gas detector system 10 advantageously detects gaseous species (contaminants) which are suitably contained in a gas sample. In general, pumping laser driver system A pumps ILS laser 500, preferably at or near (but above) the threshold level such that a laser beam passes through the gas sample thereby enabling the spectrum of the gas sample to be obtained. This spectrum is suitably detected through use of detector/computer system D, which, upon manipulation, enables the reliable and accurate determination of the presence and concentration at high sensitivity levels of gaseous species (contaminants) which may be contained within the gas sample.

Figure 2B:
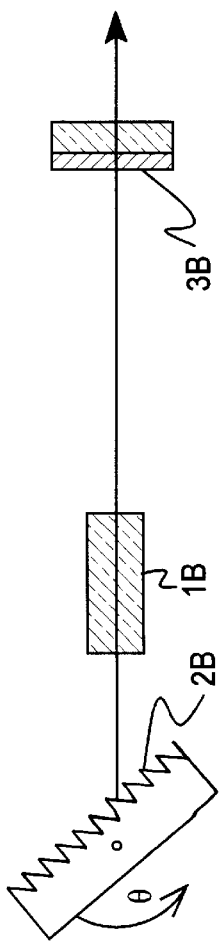
Figure 2C:
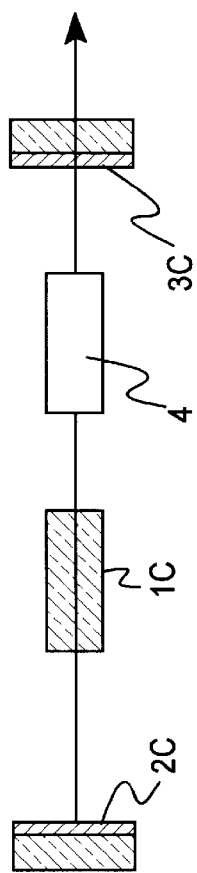

With reference to FIGS. 2A–2C, and in order to more fully explain the scientific principles utilized in accordance with the present invention, the general principles of intracavity laser spectroscopy (ILS) are illustratively shown. As is known, in its simplest terms, a laser can be described as containing a gain medium, in which optical gain is produced, and a resonator, comprised of optical elements such as mirrors. Optical losses may appear in both the medium and the optical elements comprising the laser cavity (e.g., the resonator). With particular reference to FIG. 2A, a laser device in its simplest form can be schematically illustrated as including a gain medium 1A around which respective mirrors 2A and 3A are placed. Mirrors 2A and 3A are typically coated to have high reflectivity surfaces over a broad spectral range. For example, the mirror coating on mirror 2A may be totally reflective, while the mirror coating on mirror 3A may be partially reflective thereby permitting some light to escape from the laser cavity. The spatial region between the reflective surfaces of mirrors 2A and 3A in which the gain medium 1A is placed defines the laser resonator or cavity, and in the context of the present invention relates to the so-called "intracavity region."

The intensity (I) of the laser output may be determined both by the wavelength region ($\lambda$) over which the gain medium 1A operates and the reflectivity of the resonator elements (e.g., mirrors 2A and 3A). Normally this output is broad and without sharp, distinctive spectral features, as is shown in the plot of intensity (I) versus wavelength ($\lambda$) provided in FIG. 2D, which corresponds to the laser of FIG. 2A.

Figure 2D:
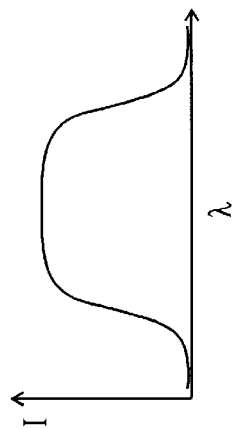
FIGS. 2D–2F are graphs that represent the accompanying graphical spectral outputs (intensity versus wavelength) obtainable from the devices depicted in FIGS. 2A–2C, respectively.
Figure 2E:
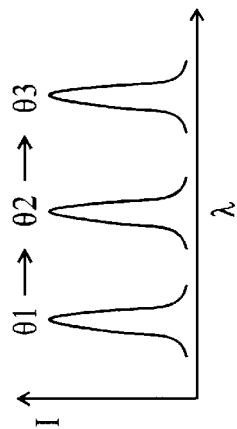

By selecting different optical elements to form the laser cavity, the spectral output of the laser can be altered or "tuned." For example, and with particular reference to FIG. 2B, a tuned resonator cavity may include a diffraction grating 2B which replaces the highly reflective mirror 2A shown in FIG. 2A. As shown, the laser device therefore includes diffraction grating 2B, mirror 3B, and a medium 1B positioned therebetween. In general, the result in spectral output from this tuned laser will be narrowed and appear as wavelengths within the original spectral output of the laser defined by the gained medium 1A and the mirrors 2A and 3A of FIG. 2A. For example, a schematic plot of intensity (I) versus wavelength ($\lambda$) illustrating a narrowed output is depicted in FIG. 2E.

Figure 2F:
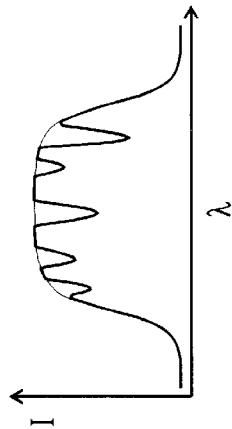

The laser output can also be altered by placing gaseous molecules, atoms, radicals, and/or ions in either their ground or excited states inside the optical resonator (e.g., cavity). With reference to FIG. 2C, a laser so configured may include a highly reflective mirror 2C, a partially reflective mirror 3C with a medium 1C, and an intracavity absorber 4 placed therebetween. In this case, intracavity absorber 4 may comprise such gaseous species (e.g., the sample containing contaminants). The effect of the intracavity gaseous species on the laser output can be observed. For example, a plot of I versus $\lambda$ for such a device is shown in FIG. 2F. FIG. 2F comprises an absorption spectrum of the gaseous species contained within intracavity absorber 4. The distinct absorption features illustrated in FIG. 2F arise from the intracavity species losses against which the laser gain must compete.

Thus, the absorption spectrum of the intracavity species may appear in the spectral output of the laser. In particular, the laser output intensity (I) at wavelengths where the stronger intracavity absorption features compete effectively against the gain properties of the resonator are more reduced. As a result, as illustrated, instead of a relatively smooth continuous output, such as shown in FIG. 2D, a structured laser output such as shown in FIG. 2F may be observed. The decreases in intensity (I), as shown in FIG. 2F, are due to absorption by the gaseous intracavity species, i.e., the more intense the absorption features, the larger the decrease in the laser output intensity. In accordance with the present invention, the absorption spectrum obtained by intracavity laser measurements in which an intracavity absorber 4 is employed can be utilized for the high sensitivity detection of such gaseous species. It has been found that each gaseous species can be uniquely identified by its respective absorption spectrum (signature) and thus can be used to confidently identify such gaseous species (contaminant).

The present inventors have found that the appearance of the absorbing species (gaseous elements) within the laser resonator before and/or during the competition between gain and losses which naturally occur as the laser system approaches threshold give rise to enhanced detection sensitivity through use of ILS. In view of the fact that the losses associated with the intracavity absorber 4 become part of the competition between the gain and losses within the laser, even a small absorbance associated either with a weak absorption transition and/or an extremely small absorber concentration is amplified dramatically during the gain/loss competition. As a result, such competition clearly appears in the output of the ILS signal (see FIG. 2F). Thus, using these principles, ILS can be utilized to detect both weak absorption and/or extremely small absorber concentrations.

ILS detection differs significantly from other spectroscopy methods which employ lasers. As described above, the output of a laser used for spectroscopy typically excites in a gaseous species, a secondary phenomena which is then monitored. Alternatively, output of a laser may be passed through a gaseous species and the absorption of selected wavelengths in the output of the laser provides means for characterizing the gas. In either case, the operation of the laser is separate from and unaffected by the gaseous species being measured.

With ILS detection, however, the operation of the laser is directly affected by the gaseous species. In this manner, the ILS laser 500 itself acts as a detector. In particular, the output from the ILS laser 500 as it exits the laser cavity contains spectroscopic information about the gaseous species. This mode of operation is unique to ILS detection and the ILS laser 500.

Accordingly, ILS lasers 500 are distinctly different from conventional lasers and possess operational characteristics which are not typical of conventional lasers. For example, absorbing species which produce loss are intentionally introduced into the laser cavity of ILS lasers 500. These absorbing species affect the operation of the ILS laser 500 and alter its output.

Also, unlike lasers employed in conventional applications, ILS lasers 500 operate at or above but close to threshold (e.g., within 10% of threshold power). However, operating near threshold often causes the output of the ILS laser 500 to be unstable. Accordingly, additional techniques directed to stabilizing the output of the ILS laser 500 may be required.

In contrast, conventional lasers typically operate well above threshold to maximize output. Maximizing output, however, is not the objective of ILS lasers 500. Consequently, laser media which are inefficient and/or do not produce high output power may be employed for ILS detection when such laser media are unfavorable for most other laser applications. The purpose of the ILS laser 500 is not to produce light, but to monitor loss within the laser cavity. As described above, mode competition inside the laser cavity enables such loss within the ILS laser 500 to be detected with enhanced sensitivity.

Since ILS detection possesses increased sensitivity beyond conventional optical spectroscopy techniques, interferences from background gases having both weak absorption and/or extremely small absorber concentrations may be significant, even if such interferences are negligible with conventional spectroscopy techniques.

The detection of gases via ILS can be achieved by using a variety of laser systems. (As used herein, the laser system includes both the ILS laser 500 and the pumping source 100.) These laser systems each share several common properties which are required for extremely high detection sensitivity. Prior art has identified three such properties. First, the laser systems exhibit multimode operation near the energy threshold for operating. Second, the laser systems possess an operational wavelength bandwidth that is substantially broad relative to the absorption features of the gaseous species or contaminants (i.e., molecules, atoms, radicals, and/or ions) being monitored. Third, the laser systems maintain stable intensity and wavelength.

It will be appreciated that a variety of ILS laser systems having different physical and optical characteristics meet these above-listed criteria for extremely high detection sensitivity. The different physical and optical characteristics of the laser systems may also provide distinct advantages such as with regard to the experimental conditions (e.g., data acquisition times) under which ILS measurements are made. Additionally, these different physical and optical characteristics may influence one or more of the following: (1) the gaseous species or contaminant (i.e., molecules, atoms, radicals, and/or ions) that can be detected; (2) the respective concentrations of each gaseous species that can be determined; and (3) the practical types of samples to which detection can be applied. Examples of the latter include the total pressure of the sample, the sample size, and the environment within which the sample is contained (e.g., reactive versus stable environments).

Against the backdrop of these general principles, in the context of the present invention, the present inventors have devised a commercially viable contaminant sensor system 10 which provides enhanced detection of contaminants in gaseous samples. The contaminant sensor system 10 of the present invention possesses each of the above-mentioned properties required for extremely high sensitivity detection. Additionally, the ILS laser system of the present invention is smaller, simpler, and less expensive to construct than any ILS laser system disclosed in prior art.

Figure 3:
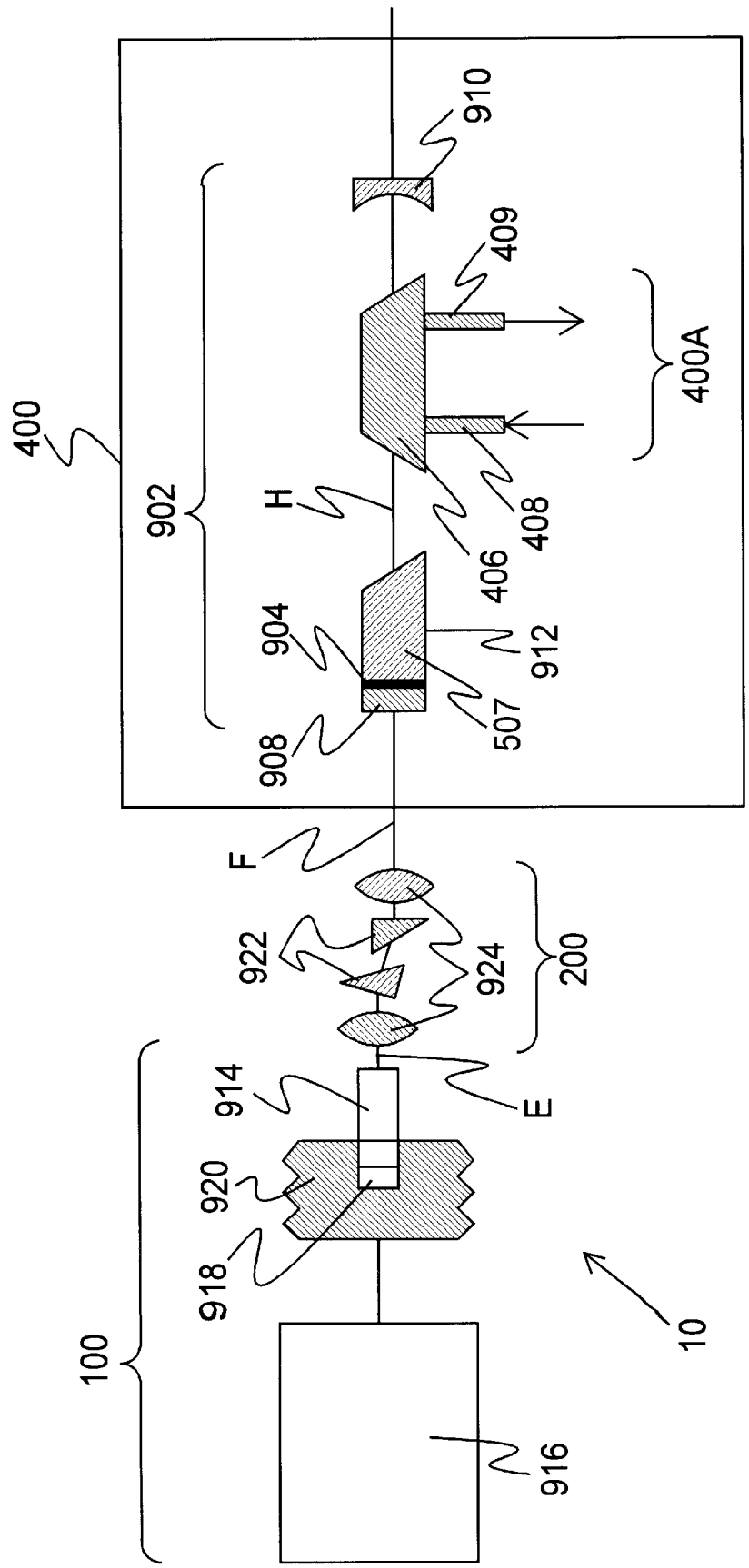
FIGS. 3 and 4 are schematic representations of an embodiment of the ILS laser of the present invention wherein the pumping source is a semiconductor laser diode.
Figure 4:
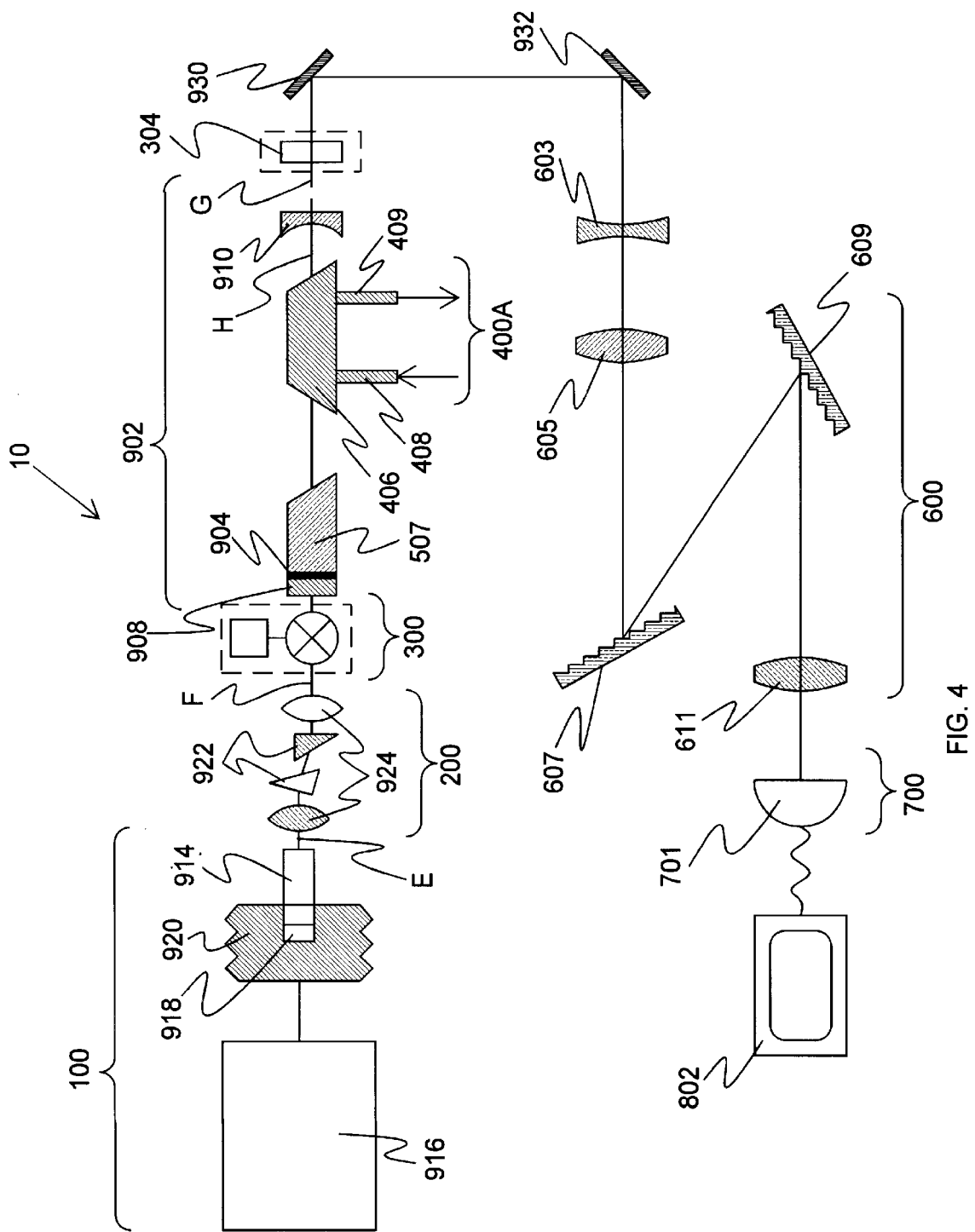

With reference now to FIGS. 1A, 3, and 4, and in accordance with an exemplary embodiment of the present invention, a detection system 10 suitably includes pump source 100, an ILS chamber assembly 400 in which ILS laser 500 is contained. Spectrometer 600 and a detector/ computer system 700, 800 are suitably optically connected to the output from the ILS laser 500 whereat the absorption spectrum is suitably manipulated, thus, enabling the high sensitivity detection of the presence and/or concentration of gaseous species (contaminants).

In order to drive ILS laser 500, system 10 requires a pumping source 100, which delivers radiation of sufficient power and within a suitable wavelength region so as to optically excite the ILS laser at or slightly above its threshold. In this regard, it is important that ILS laser 500 operate such that the gain in the laser medium exceeds the overall optical losses, including those associated with the gain medium, mirrors, and non-mirror intracavity optical elements, as well as the absorption of any gaseous species within the optical resonator cavity. Moreover, preferably laser 500 operates with multiple longitudinal modes, i.e., over a broad wavelength region. Typically, a desirable bandwidth over which laser action occurs is between about 2 and 15 nanometers (nm). While ILS laser 500 can also operate with more than one transverse resonator mode, such is not necessary. Suitably, the optical parameters (e.g., average power density, peak power density, divergence, and beam diameter) of pumping source 100, advantageously match the optical requirements of ILS laser 500. As will be appreciated, to do so it is necessary to determine how many photons can be delivered within a specific volume of the (crystal) gain medium in the ILS laser 500 and at a given distance from the pumping source 100 over a particular period of time. In general, in accordance with the present invention, such determinations are made in accordance with known theoretical and quantitative equations such that the pumping source 100 is suitably selected to advantageously match the optical characteristics of ILS laser 500.

Accordingly, a pumping source 100 is selected on the basis of its operational wavelength and on its optical parameters in a manner such that it can alone be used to excite ILS laser 500.

It should be appreciated that driver 100 may comprise any suitable optical pumping source, either coherent or incoherent, continuous or pulsed, that will suitably excite ILS laser 500. As a result, even in accordance with the present invention, pumping source 100 operates in a conventional manner and emits radiation over a desired frequency band and having a desired bandwidth.

Further in accordance with the present invention, pumping source 100 may comprise a semiconductor diode laser, a solid state crystal laser (e.g., Nd:YAG), a gas laser, one or more flashlamps, or any other pumping source operating at a wavelength $\lambda_p$ which is suitable for pumping ILS laser 500. Preferably, the pumping source 100 comprises a diode laser.

Use of a diode laser as a pump source 100, however, typically requires use of a beam shaping optics assembly 200. Disadvantageously, the output beam of a diode laser is highly asymmetric and/or astigmatic as is known in the art. Consequently, the volume of the pumping radiation from diode laser pump laser 100 that is transferred to the gain medium (i.e., crystal 507) does not suitably match the volume that must be optically excited within the gain medium of ILS laser 500. As will be described in greater detail hereinbelow, beam modification optics, such as beam shaping assembly 200, can be utilized to facilitate optical matching between a pump source 100 comprising a diode laser and the ILS laser 500; that is, to optimize the radiation delivered to ILS laser 500 by focusing the required photon density into the correct location and volume of the gain medium of the ILS laser. Specifically, beam modification system 200 is used to alter the pumping radiation of driver 100 to meet the requirements of laser 500. To correct the astigmatism, asymmetry, and divergence associated with the output beam (beam E) of a diode laser pump laser 100, normal macroscopic optics and/or micro-optics that are placed within several micrometers of the semiconductor diode laser may be employed. Examples of beam modification optics include diffractive optics, refractive optics, fiber optics (e.g., fiber optic coupler), gradient index optics wherein the refractive index varies axially, gradient index optics wherein the refractive index varies radially, and combinations thereof (e.g. gradient index optics and a fiber optic coupler). Specific examples of macroscopic optics which may be employed to shape the output beam (beam E) of a diode laser include a beam expanding telescope or alternatively, a pair of anamorphic prisms or cross cylindrical lenses.

In accordance with the present invention, the gas detection system 10 comprises an ILS laser 500 having a simplified laser cavity. The laser cavity is formed between two mirrors and has a substantially linear configuration, which does not provide astigmatic compensation. However, the linear cavity design employed by the present invention enables a gas detector system 10 to be constructed which is substantially smaller, lighter, and simpler than prior art ILS systems. Consequently, the gas detector system 10 of the present invention is less expensive to construct as well as easier to operate than other ILS laser designs. Additionally, the gas detection system 10 of the present invention can be constructed to be more rugged or mechanically stable as is required by many practical applications.

Referring, in particular, to FIG. 3, a gas detection system 10 of the present invention is depicted comprising an ILS laser 500 with a laser cavity 902 which is a linear laser cavity. By "linear laser cavity" or "linear laser resonator" is meant a laser cavity (or laser resonator) 902 that is equivalent to a laser cavity formed between only two mirrors.

In its simplest form, a linear laser cavity comprises a laser cavity 902 formed between only two mirrors: a first mirror and a second mirror. It will be appreciated that any number of additional mirrors that are planar may be included to steer (i.e., alter the path) of a beam that travels from the first mirror to the second mirror. The inclusion of these additional planar beam steering mirrors, however, does not modify the shape of the beam within the laser cavity 902 (provided that the distance between the first mirror and the second mirror is not changed). Accordingly, additional planar mirrors may be included in a laser cavity 902 of a laser that do not affect the operation of the laser but merely alter the manner in which the laser is physically configured. Consequently, a laser cavity 902 formed between a first mirror and a second mirror, having additional planar mirrors included therein to steer the beam that travels from the first mirror to the second mirror, is equivalent to a laser cavity formed solely with the first mirror and the second mirror; removing these additional planar mirrors alters neither the shape of the beam nor the operation of the laser. Rather, removing these additional planar mirrors would return the laser cavity 902 to its essentially linear configuration where the beam within the laser cavity would traverse an essentially straight path between the two mirrors, and the optical components therein would be aligned along the linear path so that the beam passes through each of them. The use of such planar steering mirrors described above, however, may be employed to fit a laser cavity 902 into a package having spatial constraints.

In contrast, intentionally introducing non-planar, i.e., curved, folding mirrors designed to provide astigmatic compensation results in a laser cavity 902 that is not a linear laser cavity as defined herein. (See, e.g., U.S. Pat. No. 5,742,054 cited above that shows an astigmatically compensated three-mirror cavity formed using a pump mirror, a curved folding mirror, and an output mirror.) The curved folding mirror changes the shape of the beam within the laser cavity 902. Similarly, any laser cavity 902 that is equivalent to a cavity having a convex or concave folding mirror is not a linear laser cavity as defined herein. It will, therefore, be appreciated that a laser cavity 902 that is a linear laser cavity can only be formed using at most two curved mirrors.

In accordance with an aspect of the present invention, the ILS laser 500 comprises an ion-doped crystal 507 which resides within a laser cavity 902 which is a linear laser cavity. An ILS laser 500 comprising an ion-doped crystal 507 within a linear laser cavity 902 is a completely novel ILS design, which has not been disclosed in prior art. It will be appreciated that the ILS laser 500 of the present invention, which is based on a linear cavity 902, requires fewer and simpler optical components than prior art designs.

The ion-doped crystal 507 in the ILS laser 500 may comprise, e.g., $Tm^{3+},Tb^{3+}$:YLF or $Tm^{3+}$:YAG, and preferably operates at or near room temperature. Other suitable ion-doped crystals 507 may also be employed in the practice of the present invention. The ion-doped crystals 507 may comprise, for example, other ion-doped vibronic laser crystals. Examples of ion-doped crystals 507 suitably employed in the ILS laser 500 of the present invention are listed in Table 1. It will be readily apparent to those skilled in this art, however, that other ion-doped crystals 507 may be employed as is suited to the particular use contemplated. Examples of other laser crystals that can be suitably employed in the present invention include aluminum oxide doped with titanium ions, $Ti^{3+}$:$Al_2O_3$, and barium lithium fluoride doped with nickel ions, $Ni^{2+}$:$BaLiF_3$. A laser crystal comprising $Ti^{3+}$:$Al_2O_3$ outputs light having a wavelength between 0.680 to 1.100 micrometers when pumped with light having a wavelength of 0.500 micrometers. A laser crystal comprising $Ni^{2+}$:$BaLiF_3$ outputs light having a wavelength between 1.3 to 1.6 micrometers when pumped with light having a wavelength of 0.680 micrometers. Additionally, $Tm^{3+}$:$YVO_4$, which emits light having a wavelength of 2 micrometers when pumped with light having a wavelength of 0.800 micrometers, as well as $Nd^{3+}$:$YVO_4$, $Nd^{3+}$:YLF, and $Nd^{3+}$:YAG, which are pumped with light having a wavelength of 0.808 micrometers, may be employed in the present invention. Accordingly, it is not intended that the ion-doped crystals 507 specifically disclosed herein, including those listed in Table 1, are to be exhaustive.

TABLE 1

LIST OF LASER CRYSTALS THAT CAN BE OPTICALLY PUMPED BY THE OUTPUT OF A DIODE LASER

| Crystal (gain medium) | Operating Wavelength of ILS laser (in $\mu$m) | Pump Laser Wavelength, $\lambda_p$ (in $\mu$m) |
|---|---|---|
| Cr: Tm: Ho: YAG | 2.10 | 0.781 |
| $Cr^{4+}$: YSO | 1.35 to 1.55 | 0.980 |
| $Cr^{4+}$: YAG | 1.38 to 1.53 | 0.980 |
| $Cr^{4+}$: YSAG | 1.30 to 1.62 | 0.980 |
| Er: GSGG | 2.80 | 0.970 |
| $Er^{3+}$: YLF | 3.40 to 3.54 at 77K | 0.970 |
| $Er^{3+}$: YLF | 2.70 to 2.95 | 0.970 |
| $Er^{3+}$: $Yb^{3+}$: Glass | 1.532 to 1.534 | 0.970 |
| $Ho^{3+}$: YSGG | 2.080 to 2.089, 2.10 | 0.780 |
| $Ho^{3+}$: $Tm^{3+}$: LUAG | 2.10 | 0.781 |

TABLE 1-continued

LIST OF LASER CRYSTALS THAT CAN BE OPTICALLY PUMPED BY THE OUTPUT OF A DIODE LASER

| Crystal (gain medium) | Operating Wavelength of ILS laser (in $\mu$m) | Pump Laser Wavelength, $\lambda_p$ (in $\mu$m) |
|---|---|---|
| $Tm^{3+}$: $Ho^{3+}$: YLF | 2.10 | 0.780 |
| $Tm^{3+}$: $Ho^{3+}$: YAG | 2 | 0.780 |
| $Tm^{3+}$: Ca Y SOAP | ~1.65 to 2.0 | 0.780 |
| $Tm^{3+}$: YLF | 2.295 to 2.424 | 0.780 |
| $Tm^{3+}$: $Tb^{3+}$: YLF | 1.449 to 1.455 | 0.780 |
| $Tm^{3+}$: Glass | 2.25 to 2.50 | 0.780 |
| $Tm^{3+}$: Ca La SOAP | 2 | 0.780 |
| $Tm^{3+}$: YOS | ~1.7 to 2.1 | 0.780 |
| $Tm^{3+}$: YSGG | 1.85 to 2.14 | 0.780 |
| $Tm^{3+}$: YAG | 1.85 to 2.16 | 0.780 |
| $Tm^{3+}$: $Ho^{3+}$: YLF | 2.31, 2.08 | 0.790 |

Referring now to Table 1, a list of crystals that can be optically pumped by a diode laser pump laser 100 is provided. The crystals comprise a host material doped with ions. The host materials listed include the following: YAG, yttrium aluminum garnet ($Y_3Al_5O_{12}$); YSO or YOS, yttrium orthosilicate ($Y_2SiO_2$); YSAG, yttrium scandium aluminum garnet ($Y_3Sc_2Al_5O_{12}$); GSGG, gadolinium scandium gallium garnet ($Gd_3Sc_2Ga_3O_{12}$); YLF, lithium yttrium fluoride ($LiYF_2$); YSGG, yttrium scandium gallium garnet ($Y_3Sc_2Ga_3O_{12}$); LUAG, lutetium aluminum garnet ($Lu_3Al_5O_{12}$); Ca Y SOAP, calcium yttrium oxyapatite silicate (Ca $Y_4(Si_2O_3)_4O$); Ca La SOAP, calcium lanthanum oxyapatite silicate (Ca $La_4(Si_2O_3)_4O$); and glass. The dopant ions include Cr, chromium; Tm, thulium; Ho, holmium; Tb, terbium; and Er, erbium. As discussed above, neodymium, Nd, may also be used as a dopant ion. Accompanying the crystals listed in Table 1 is a wavelength corresponding to the pumping radiation and a wavelength or wavelengths corresponding to the resultant output from the crystal.

As depicted in FIG. 3, the ion-doped crystal 507 has one end 904 which has a reflective coating deposited thereon. Another end 906 of the ion-doped crystal 507 is cut at an angle between about 2° to 3° to reduce interference effects. (It is conceivable that the end 906 of the ion-doped crystal 507 is cut at Brewster's angle, however, only in the case where the ion-doped crystal is large enough to accommodate such a cut). The linear laser cavity 902 as shown in FIG. 3 is formed between a first mirror (pump mirror) 908 and a second mirror (output mirror) 910. The first mirror 908 comprises the reflective coating deposited on the one end 904 of the ion-doped crystal 507. The second mirror 910 comprises a curved reflector. The laser cavity 902 is a linear laser cavity as defined above, since it is formed between only two mirrors.

The ion-doped crystal 507 is pumped by pump beam F which is shown in FIG. 3 as incident on the one end 904 which has a reflective coating deposited thereon. Accordingly, the ion-doped crystal 507 is optically pumped. The output beam from the ion-doped crystal 507 (beam H) exits the laser medium through the other end 906 of the ion-doped crystal which is cut at an angle to reduce interference effects as discussed above. The output beam from the ion-doped crystal 507 (beam H) extends across the linear laser cavity 902 to the second mirror 910. (It will be appreciated that due to refraction, the beam, i.e., beam H, within the linear laser cavity 902 is bent slightly, e.g., between about 2° to 3°, at the end 906 of the ion-doped crystal 507 when the ion-doped crystal is cut at a small angle, e.g., between about 2° to 3°.)

It will further be appreciated that longitudinal optical pumping is employed to pump the ILS laser 500 depicted in FIG. 3. The terms longitudinal optical pumping, longitudinal pumping, and longitudinally pumped are used herein in their conventional meaning, which is well-known in the art. Specifically, the pump beam F, incident on the one end 904, is directed along the linear laser cavity 902 in about the same direction as the output beam from the ion-doped crystal 507 (beam H), which extends across an axis running through the laser cavity from the first mirror 908 to the second mirror 910 (or in the about the same direction as the beam within the ion-doped crystal). It will be appreciated that the ion-doped crystal 507 typically has a symmetric axis extending from the one end 904 to the other end 906. Longitudinal pumping corresponds to pumping in a direction parallel to the symmetric axis of the ion-doped crystal 507. Analogously, an ion-doped crystal 507 which is pumped by a pump beam directed along the linear laser cavity 902 and in approximately the same direction as the output beam from the ion-doped crystal 507 (beam H), which extends across the laser cavity 902 to the output mirror 910 (or in the about the same direction as the beam within the ion-doped crystal), is said to be longitudinally pumped.

Alternatively, transverse optical pumping may be employed to pump the ILS laser 500 of the present invention. The terms transverse optical pumping, transverse pumping, and transversely pumped, are used herein in their conventional meaning, which is well-known in the art. In particular, the ion-doped crystal 507 may be pumped by a pump beam which is incident on a side of the ion-doped crystal such as side 912 shown in FIG. 3. Transverse optical pumping corresponds to the case where the pump beam, i.e., the output of the pumping source 100, which is incident ion-doped crystal 507, is directed perpendicular to the symmetric axis of the ion-doped crystal. With transverse optical pumping, the pump beam is directed approximately perpendicular to the output beam from the ion-doped crystal 507 (beam H), which extends across an axis running through the linear laser cavity 902 from the first mirror 908 to the second mirror 910. In particular, an ion-doped crystal 507 which is pumped by a pump beam incident on a side of the ion-doped crystal 507, such as side 912, is said to be transversely pumped. Similarly, an ion-doped crystal 507 which is pumped by a pump beam which is directed approximately perpendicular to the direction of the output beam from the ion-doped crystal 507 (beam H), which extends across the linear laser cavity 902 to the output mirror 910, is also said to be transversely pumped.

When the pumping source 100 comprises a semiconductor diode laser or a solid state crystal laser (e.g., Nd:YAG), longitudinal pumping may be employed. Alternatively, flashlamps or diode lasers can be employed in transverse pumping. It will be appreciated that with transverse pumping, a plurality of flashlamps configured to pump from more than one side of the ion-doped crystal 507, may be used as the pumping source 100.

With continued reference to FIG. 3, in some applications, it may be necessary that the incoming beam be appropriately focused into the laser medium (e.g., ion-doped crystal or glass) 507 within ILS laser 500. In accordance with a particularly preferred aspect of the present invention, a focusing lens (not shown) suitably comprising an optical focusing lens with an AR coating centered about a wavelength $\lambda_p$ is employed.

ILS laser 500, in the simplest case, comprises an optical resonator cavity 902 defined by the entire optical path length between respective mirrors 908 (first mirror) and 910 (second mirror). In those cases where system 10 is used to detect gases (contaminants) within a sample which does not chemically react with the components of the laser itself (e.g., gain medium or crystal 507, mirrors, mechanical mounting, and the like), the resonator cavity can be defined by the region between mirrors 908 and 910. In such a case, the gas sample region (i.e., the region where the gas sample resides) comprises the region between mirrors 908 and 910 (excluding the laser crystal 507).

However, for samples which do chemically react with one or more of the laser components (e.g., a corrosive or reactive gas), it is desirable to separate the gas sample region from such components. In accordance with a preferred embodiment of the present invention, a separate sample system 400A may be advantageously utilized to isolate the sample from the laser components.

In accordance with this preferred aspect of the present invention, sample system 400A preferably comprises a gas sample cell body 406 suitably maintained within a gas sample cell holder (not shown). Respective cell windows 404 and 405 are suitably mounted on the distal ends of gas sample cell body 406 and provide optical access to the sample within the cell body. Windows 404 and 405 also suitably seal cell body 406. An inlet conduit 408 and an outlet conduit 409 are operatively connected to gas cell body 406.

Couplings 408 and 409 are advantageously employed to ensure efficient and effective passage of a gas sample into and out of gas (contaminant) sample cell system 400A. Accordingly, the gas detector system 10 of the present invention can continuously monitor a flowing gas at variable pressures including high pressure. In particular, the use of the gas sample cell body 406 advantageously enables the operation of the ILS laser 500 when measuring gases having a pressure which is different (i.e., higher or lower) than atmospheric pressure or than the pressure for which the ILS laser was designed to operate. Without such a gas sample cell body 406, lasing would be difficult to achieve when monitoring a gas sample having a different pressure from the pressure at which the ILS laser 500 was aligned. Thus, the gas sample cell body 406 allows stable operation of the ILS laser 500 for a gas sample having a pressure in excess of atmospheric pressure or the pressure which the ILS laser was designed to operate. Alternatively, the gas sample may have a pressure less than atmospheric pressure or the pressure which the ILS laser 500 was designed to operate (e.g., when a vacuum exists in the gas sample cell body 406). Additionally, the gas sample cell body 406 enables stable operation of the ILS laser 500 for a gas sample having a pressure which fluctuates.

Suitably, cell body 406 comprises a stainless steel or aluminum body having dimensions suitably in the range of 10 to 90 millimeters (mm). Preferably, the body 406 has an opening therein which is symmetrically in the center of gas sample cell body 406. Preferably, the diameter of the opening in cell body 406 is suitably selected to be significantly larger than the diameter of the incoming beam such that optical alignment of gas sample system 400A may be easily obtained.

The thickness of windows 404, 405 is suitably selected to avoid interferometric effects which may interfere with the quality of the ILS absorption spectrum obtained through operation of the gas detection system 10. In accordance with this aspect, the material used in forming windows 404, 405 is optimally chosen to minimize absorption losses in the region over which ILS laser 500 operates. Windows 404, 405 may be formed from an optically compatible material, such as Infrasil™, which is readily available. Windows 404, 405 are suitably oriented at Brewster's angle and have antireflection coatings so as to further minimize reflective losses from the window surfaces.

As so configured, gas sample cell 406 suitably permits beam H to pass through the gaseous sample to be analyzed. Couplers 408, 409, are suitably selected to provide easy adjustment such as may be required to realign and/or align windows 404, 405 within ILS laser 500 without significantly altering the threshold pumping conditions. The resonator cavity 902, in the case where system 400A is employed, is suitably defined by the physical length between mirrors 908 and 910 (including the laser crystal 507 and including the region between windows 404, 405 as well as windows 404 and 405 themselves that comprise the sample system 400A).

In the event that system 400A is present within chamber 400, it is necessary that any gases (contaminants) within chamber 400 that are to be detected are suitably removed or eliminated such that the absorption spectrum of the sample obtained through use of the gas detection system 10 is accurate as to the amount or presence of those gases (contaminants) within the gas sample contained within the sample system. In accordance with a preferred aspect of the present invention, chamber 400 advantageously evidences a sealed container, which can be either purged of gas(es) (contaminant(s)) to be detected, or evacuated to remove gas(es) (contaminant(s)) to be detected, or in which the level of gas(es) (contaminant(s)) can otherwise be reduced below the level to be detected in the sample system 400A. Continuous removal of the contaminants can be achieve, for example, by gettering or active ion pumping, as described more fully below.

More particularly, reducing gases (contaminants) in chamber 400 (excluding sample system 400A) to an acceptable level may suitably comprise purging or evacuating the chamber such that the level of gases (contaminants) is below that to be detected in the gas sample within system 400A. It will be appreciated that the loss contributed by the gases in the chamber 400 will be comparable to loss contributed by the gases in the gas sample cell body 406 when the ratio between (1) the concentration of gases in the chamber and (2) the concentration of gases in the gas sample cell body is equal to the ratio between (1) the length that the ILS laser beam traverses in the cell body and (2) the length of the cavity (i.e., between mirror 908 and mirror 910).

In such cases where the contaminant comprises water vapor, it is necessary that water levels in chamber 400 be reduced below those which are contained within the sample. In accordance with the present invention, detection levels of up to 10 parts per trillion (ppt) are obtainable. While any now known or hereafter devised method for removing contaminants (e.g., water) from chamber 400 (excluding the sample system 400A) can be practiced within the context of the present invention, preferably, the chamber is appropriately sealed and inert gases, such as nitrogen are pumped therein. In some instances, it may be necessary to further evacuate the chamber 400 so as to create a vacuum which removes substantially all contaminants contained therein. Also, it may be useful to heat the chamber 400 while evacuating. Application of such heating or "baking" will enable a higher level of vacuum to be achieved if the chamber 400 is subsequently cooled while continually being evacuated. In accordance with yet a further aspect of the present invention, a getter (not shown) may be advantageously employed with chamber 400 to provide even further elimination of water within the chamber and/or to effectively maintain a low water concentration within the chamber that has been previously achieved by another method such as evacuation. As will be appreciated by those skilled in the art, a getter (e.g., a molecular sponge) having the capacity for continuously absorbing/adsorbing water may be utilized to reduce and/or maintain the level of water (contaminants) below the water concentration that is to be detected in the gas sample cell 404–406 (e.g., 10 ppt).

Alternatively, ion pumping (not shown) may be advantageously employed with chamber 400 to provide further elimination of water within chamber 400 and/or to effectively maintain a low water concentration within the chamber that has been previously achieved by another method. As will be appreciated by those skilled in the art, an ion pump having the capacity for continuously absorbing/adsorbing water may be utilized to reduce and/or maintain the level of water (contaminants) below the water concentration that is to be detected in the gas sample cell 404–406 (e.g., 10 ppt).

The sample is suitably communicated to system 400A by connecting a gas line to connectors 408, 409 and feeding the gas into the sample system (for example, when the sample comprises a corrosive gas).

However, in such cases where the sample does not chemically react with the laser components, the gas sample region may nominally be defined by the physical region between mirrors 908 and 910 (excluding laser crystal 507). A sample is suitably communicated into the chamber 400 itself (for example, when the sample comprises a non-corrosive gas).

As briefly mentioned above, ILS sensor 500 suitably optically detects gaseous species (contaminants, e.g., water vapor) contained in a sample placed within chamber 400. In accordance with the present invention, ILS laser 500 suitably comprises a crystal 507 mounted in a crystal holder (not shown). Crystal 507 is suitably mounted in the crystal holder such that the crystal also is optimally placed with reference to the incoming optical pumping beam. As previously briefly mentioned, the incoming optical beam is suitably shaped through use of beam shaping assembly 200 such that incoming beam F suitably matches the mode volume of the ILS gain medium (e.g., crystal 507).

It will be appreciated, however, that the distance between any reflective surfaces (e.g., mirrors and windows) within the ILS laser 500 must not be such that any interference occurs inside the ILS laser. Interference patterns are produced if the distance between the reflective surfaces equals an integer number of wavelengths comparable to the wavelength at which the ILS laser crystal 507 operates.

ILS laser crystal 507 preferably operates in a wavelength region suitable for detection of the contaminants contained within the gas sample (e.g., water vapor) over which a signature absorption spectrum can be obtained. As previously mentioned, laser crystal 507 generally exhibits the properties of a multimode laser system. It will be appreciated that the mode spacing of output of the laser crystal 507 is required to be small enough to accurately represent the absorption features of the gas sample. Light produced by laser crystal 507 preferably has a mode spacing of less than about 1 gigahertz (GHz), thus, ensuring accurate spectral replication of absorption bands. A particularly preferred laser medium comprises a crystal 507 cut at a small angle (e.g., 2° to 3°) to minimize interference effects, as described above.

Laser crystals currently available, while improving in efficiency, have considerable losses associated with them. The losses translate to heat. In accordance with the present invention crystal 507 suitably is mounted in a manner allowing for the effective removal of the heat thus generated in operation. It should be appreciated, however, that as the efficiency of laser crystals continue to improve as new crystals are developed, the need or requirements on heat removing devices will be reduced and likely, at some point, the losses will be small enough that the need to remove the heat may be eliminated all together. However, using crystals presently available, ILS laser system 500 preferably further comprises a heat sink system (not shown).

In accordance with a preferred aspect of the present invention, optical excitation of the ion-doped crystal 507 is provided by pumping source 100 which comprises a semiconductor diode laser 914 as shown in FIG. 3. The semiconductor diode laser 914 is powered by an electrical power supply 916 and cooled by thermoelectric cooler 918. The semiconductor laser diode 914 and the thermoelectric cooler 918 are mounted in a heatsink 920 provided to dissipate heat generated by the semiconductor diode laser.

As described above, the output beam (beam E) of the semiconductor diode laser 914 is highly asymmetric and/or astigmatic. To correct the asymmetry and/or astigmatism associated with the output beam (beam E) of the semiconductor diode laser 914, beam shaping assembly 200 is employed. The beam shaping assembly 200 enables the output beam (beam E) of the semiconductor diode laser 914 to be optically matched to the mode volume of the ILS gain medium (i.e., the ion-doped crystal 507) contained within the ILS laser 500. FIG. 3 shows the beam shaping assembly 200 comprising macroscopic optics which include a pair of anamorphic prisms 922 and a pair of lenses 924. Alternatively, a beam expanding telescope, fiber optics, gradient index optics, or micro-optics that are placed within several micrometers of the semiconductor diode laser 914 may be employed.

As will be appreciated by those skilled in the art, the quality of the quantitative information obtainable through use of the gas detection system 10 depends, at least in part, on stable operation of ILS laser 500. In the context of the present invention, the stability of ILS laser 500 depends directly on how reproducibly the ILS laser reaches threshold. Desirably, pumping source 100 suitably pumps ILS laser 500 continuously near threshold where its greatest sensitivity may be obtained. However, not all drivers are capable of reliably operating in a continuous fashion. In addition, operating continuously tends to require substantial effort to maintain amplitude and wavelength stability of the ILS laser 500, which may have an adverse impact on cost and thereby produce an adverse impact on the commercial viability of the gas detection system 10.

As an alternative to operating ILS laser 500 in a continuous mode (cw), and in accordance with a preferred embodiment of the present invention, the ILS laser is operated in a "pulsed mode" or a "chopped mode". As used herein, the terms "pulsed mode" and "chopped mode" refer to processes for reproducibly exposing ILS laser 500 (i.e., ion-doped crystal 507) to pumping radiation such that the ILS laser will be switched on and off. Chopping corresponds to causing the pump radiation to alternate between zero intensity and a fixed intensity value at a fixed frequency and over a fixed (often symmetric) duty cycle. In contrast, pulsing corresponds to causing the pump radiation to alternate between zero intensity and a non-zero intensity (which is not necessarily fixed) over a duty cycle which may be varied and which is typically asymmetric. (Alternatively, the pump radiation can be modulated such that the intensity of the pump beam does not reach zero intensity but fluctuates alternately between at least two intensity levels which brings the ILS laser 500 alternately above and below threshold.)

Through operation in the chopped mode or the pulsed mode, stable operation of ILS laser 500 consistent with the quantitative spectral and concentration measurements may be obtained in a commercially viable manner. Preferably, the ILS laser 500 is operated in the pulsed mode or the chopped mode or is otherwise modulated. Operation in the continuous mode, however, can be utilized for certain circumstances.

As described above, the pulsed mode or the chopped mode have been shown to provide advantages with respect to stability and detection sensitivity. Such intensity modulation (e.g., interruption) can be achieved utilizing, among other things, a mechanically operated chopper, an acousto-optic modulator, a shutter, and the like.

As shown in FIG. 4, a mechanical or electro-optic (e.g., acousto-optic) modulator 926 can be inserted between the pumping laser beam F and the ion-doped crystal 507. The mechanical or electro-optic modulator 926 is powered and controlled by a modulator driver 928.

Alternatively, the output intensity of pumping source 100 may be modulated instead of secondarily chopping the output beam (beam E). For example, in the case where the pumping source 100 comprises a semiconductor diode laser 914, the electrical power from the power supply 916 to the semiconductor diode laser can be pulsed or modulated. Alternating voltages to the semiconductor diode laser 914 are provided which thereby cause the output of the semiconductor diode laser to fluctuate between high and low intensity levels. The high and low intensity levels of the output of the pumping source 100 are such that the ion-doped crystal 507 is optically excited just above and below the threshold required for lasing. The ILS laser 500 is consequently turned on and off.

While any now known or hereafter devised manner of producing the chopped mode or the pulsed mode can be utilized in accordance with the present invention, advantageously such modes are obtained through use of modulation assembly 300. Desirably, modulating device 300 does not steer the pumping beam and is synchronized to modulate the intensity of the ILS laser 500 output beam exiting chamber 400.

In accordance with this aspect of the present invention, beam E is periodically prevented from reaching ILS laser 500 by the modulation assembly 300, which periodically blocks and transmits the pumping laser beam E. It should be appreciated that the modulation assembly 300 may comprise a variety of devices, e.g., mechanical or electro-optical, which periodically blocks or modulates the pumping laser beam. As previously mentioned, in accordance with the present invention, the intensity of the pumping radiation emanating from pumping source 100 must only fall below that required to make ILS laser 500 reach threshold and therefore, is not required to reach a zero value.

With either the pulsed mode or chopped mode, the output of ILS laser 500, which contains the absorption information, may be periodically sampled. Advantageously, the output beam E from the pumping source 100 is modulated, while modulation device 304 suitably modulates the output beam of ILS laser 500 that exits chamber 400, thereby periodically sampling the output of the ILS laser. Modulation assembly 300 alternatively blocks pumping beam E from reaching ILS laser 500 gain medium (e.g., crystal 507), while modulator 304 alternatively blocks ILS laser beam G exiting chamber 400 from reaching both spectrometer 600 and detector 700. ILS laser 500 output exiting chamber 400 is suitably directed to modulator 304.

FIG. 4 shows that the output of the ILS laser 500 (beam G) having passed through the gaseous species to be monitored is directed to a spectrometer assembly 600. Prior to reaching the spectrometer assembly 600, however, the output of the ILS laser 500 (beam G) passes through modulation device 304.

In accordance with various aspects of the present invention, modulator 304 comprises an acousto-optic modulator. It should be appreciated, however, that other available devices, for example, another mechanically operated chopper or even a shutter may be suitably employed for this purpose. As discussed above, to extract quantitative information from the ILS laser 500 exiting beam, modulator 304 periodically samples the output of ILS laser, which contains the absorption data of contaminants (e.g., gaseous species) contained in the particular sample.

Advantageously, pumping laser beam F is modulated, while modulation device 304 suitably modulates the output beam of ILS laser 500 that exits the laser cavity 902, thereby periodically sampling the output of the ILS laser. Modulator 926 alternatively blocks pumping beam F from reaching ILS laser 500 gain medium (e.g., crystal 507), while modulator 304 alternatively blocks the beam exiting the laser cavity 902 (beam G).

It will be appreciated that instead of employing modulator 304, detector assembly 700 may be alternately switched on and off to periodically sample the output of ILS laser 500.

While the specific form of modulation is variable, use of modulation enables generation of a reproducible, effective optical path length within ILS laser 500. Stated another way, by varying the generation time ($t_g$), i.e., the time period over which intracavity mode competition within ILS laser 500 is permitted to occur, the effective absorption path length within the intracavity resonator can be controlled and selected to achieve optimum quantitative application of the ILS gas detector 10.

Modulation of the output of the semiconductor diode laser 914 is synchronized with modulation device 304 such that quantitative information from ILS laser 500 can be extracted in a time-resolved manner. Pump beam F is effectively delivered to ILS laser 500 (i.e., ion-doped crystal 507) intermittently by passing pump beam F through modulation assembly 300. Delivering radiation intermittently alternately brings ILS laser 500 near threshold and below threshold. After the generation time, $t_g$, elapses with ILS laser 500 at or slightly above its threshold, the ILS laser output is deflected by modulator 304 to the entrance of spectrometer assembly 600 and detector assembly 700 for detection. However, ILS laser 500 output beam G is deflected to spectrometer 600 and detector 700 for only a short time interval determined by the synchronization of modulation assembly 300 and modulation device 304. The synchronization of modulation assembly 300 and modulation device 304 ensures that radiation from ILS laser 500 is sampled over a well-defined time interval ($t_g$). The time interval between when the output of the semiconductor diode laser 914 is not interrupted by the modulation assembly 300 and when modulator 304 opens is determined by $t_g$.

Synchronization of modulation assembly 300 and modulation device 304 may be achieved by several conventional methods such as, for example, through electronic control by a digital circuit (not shown) operated by computer 802 operatively connected to detector 10. Typically, synchronization of modulation assembly 300 and modulation device 304 will be suitable to obtain generation times ($t_g$) varying from a few milliseconds (msec) to about 1 microsecond ($\mu$sec) with a precision of about 1 microsecond. Such synchronization results in the modulation assembly 300 allowing the output of the pumping source 100 to pass uninterrupted when modulator 304 is closed.

The generation time, $t_g$, can be variably selected without the use of modulator 304 by pulsing the output of the pumping source 100 shown as semiconductor diode laser 914 in FIG. 4. As described above, pulsing corresponds to causing the pump radiation to alternate between zero intensity and a non-zero intensity value (which is not necessarily fixed) over a duty cycle which may be varied thereby bringing the ILS laser 500 (i.e., ion-doped crystal 507) alternately below and above (or at) threshold. Accordingly, the ILS laser 500 is turned off and on. The duration over which the ILS laser 500 operates may be varied by changing the duty cycle of the pump beam; in particular, the duration over which the pumping source 100 (e.g., semiconductor diode laser 914) pumps the ILS laser to about threshold. Accordingly, the generation time ($t_g$), i.e., the time period over which intracavity mode competition within ILS laser 500 is permitted to occur, is varied. In this case, the detector assembly 700 remains continuously activated and the output beam of the ILS laser 500, which exits laser cavity 902, is allowed to continuously reach the spectrometer assembly 600 and detector assembly.

Pulsing the output of the pumping source 100 can be achieved by externally controlling the transmission of the pump beam with a "pulser". Alternatively, the output intensity of the semiconductor diode laser 914 (i.e., pumping source 100) may be modulated by varying the electrical power supplied to the diode laser pump laser. As described above, the electrical power supplied to the semiconductor diode laser 914 can be modulated to alternately obtain optical power just above and below that required to cause the ion-doped crystal 507 to operate.

Accordingly, the gas detection system 10 of the present invention may include any of the following configurations each of which enables the generation time to be varied:

(1) The output of the pumping source 100 may be chopped with an external chopper (e.g., modulation assembly 300) and the detector 700 may be continuously activated with transmission of the output from the ILS laser 500 to the detector being controlled by a pulser (e.g., modulator 304) to enable periodic sampling;

(2) The output of the pumping source 100 may be chopped with an external chopper (e.g., modulation assembly 300) and the detector 700 may be pulsed on and off to enable periodic sampling of the output from the ILS laser 500;

(3) The output of the pumping source 100 may be pulsed with an external pulser (e.g., modulation assembly 300) and the detector 700 may be continuously activated with the duration of the interaction between the output of the ILS laser 500 and the gaseous species being controlled by the duration of the pulses from the pumping source which cause the ILS laser to operate;

(4) In the case where the pumping source 100 comprises, e.g., a semiconductor diode laser 914, the diode laser pump laser may be pulsed by varying the electrical power supplied to the semiconductor diode laser and the detector 700 may be continuously activated with the duration of the interaction between the output of the ILS laser 500 and the gaseous species being controlled by the duration of the pulses from the semiconductor diode laser which cause the ILS laser to operate;

(5) In the case where the pumping source 100 comprises, e.g., a semiconductor diode laser 914, the diode laser pump laser may be chopped by varying the electrical power supplied to the semiconductor diode laser and the detector 700 may be continuously activated with the transmission of the output from the ILS laser 500 to the detector being controlled by a pulser (e.g., modulator 304) to enable periodic sampling; and (6) In the case where the pumping source 100 comprises, e.g., a semiconductor diode laser 914, the diode laser pump laser may be chopped by varying the electrical power supplied to the semiconductor diode laser and the detector 700 may be pulsed on and off to enable periodic sampling of the output from the ILS laser 500.

In accordance with the present invention, output beam G from ILS laser 500 after passing through sample system 400A is directed to spectrometer assembly 600. Such direction can be obtained, such as shown in FIG. 4, through use of steering mirrors 930 and 932. Mirrors 930 and 932 preferably comprises plane mirrors containing a coating for high reflectivity in the desired spectral region of operation of the ILS laser 500.

With continued reference to FIG. 4, spectrometer 600 comprises dispersive gratings designed to spectrally resolve a coherent beam, in particular, the absorption spectrum of the contaminant in the sample to be detected. Suitably, the spectral dispersion of the spectrometer 600 is sufficiently large to clearly resolve the absorption features of such contaminant, thus, enabling the identification of the "signature" of each contaminant and the quantitative determination of the concentration of the contaminant. While any now known or hereafter devised spectrometer may be utilized in accordance with the present invention, preferably spectrometer 600 comprises two diffraction grating 607 and 609 operating in conjunction with an optical beam expanding assembly comprising lenses 603 and 605 and a focusing lens 611. Lens 603 preferably comprises a negative lens and lens 605 preferably comprises a collimating lens; each preferably having an AR coating centered about the absorption spectrum of the contaminant in the sample to be detected. Lens 611 also preferably having an AR coating centered about the absorption spectrum of the contaminant, focuses the output of the spectrometer onto multichannel array detector 701.

The spectral region over which the ILS laser 500 operates is dispersed by spectrometer 600 and is displaced spatially across a plane where the multichannel array detector 701 located. A computer 802 for operating and reading information from the multichannel detector 701 is operatively connected thereto. As a result, the entire spectrally dispersed absorption spectrum of the particular contaminant sought to be identified through use of the gas detection system 10 can be obtained. The positions and relative intensities of the specific absorption features of the contaminant can be utilized to uniquely identify the detected gas (contaminant) as well as quantitatively determine the amount of the gas (contaminant) so detected.

The detector 701 may comprise, for example, an InGaAs multichannel (256 pixel, 50 to 100 micrometer spacing) array detector. The light detected by the multichannel detector 701 is preferably transduced into electronic signals at each detector element (pixel) with signals thereafter transferred to an analog-to-digital (AID) converter (not shown). Once the data is so converted, it is sent to a computer 802 which may be suitably programmed to convert the electronic signals into spectral information, i.e., spectral signatures identifying a particular gas (contaminant) and concentration of gases (contaminants).

Alternatively, the output of the ILS laser 500 (beam G) having passed through the gaseous species to be monitored can be directed to a spectrometer assembly 600 having at least one dispersive optical element (e.g., diffraction gratings 607 and 609) therein which can be scanned with respect to wavelength. The output of the spectrometer assembly 600 can then be directed to a single channel detector. The spectral signature of the gaseous species in the laser cavity 902 is obtained by scanning the dispersive optical element while the light transmitted through the spectrometer assembly 600 passes through an appropriate aperture (e.g., slit) placed in front of the single channel detector. The intensity of the light transmitted through the spectrometer assembly 600, i.e., the output of the spectrometer assembly, is recorded as the dispersive optical element is scanned.

The concentration of the gaseous species can be determined from the intensity of the absorption feature(s) found in the spectral signature. It will be appreciated that the absorption feature(s) found in the spectral signature must be calibrated versus known concentrations of a specific intracavity gaseous species. Since intracavity laser spectroscopy offers increased sensitivity beyond prior art methods, weak transitions previously not measured may become measurable for the first time with the gas detection system 10 of the present invention. In such cases, these weak transitions can be used to identify the spectral signature and certify the presence of the gaseous species. Such weak transitions can also be calibrated by the gas detection system 10 thereby enabling the concentration of the gaseous species to be determined by the intensity of the absorption feature(s) corresponding to these weak transitions.

Figure 5:
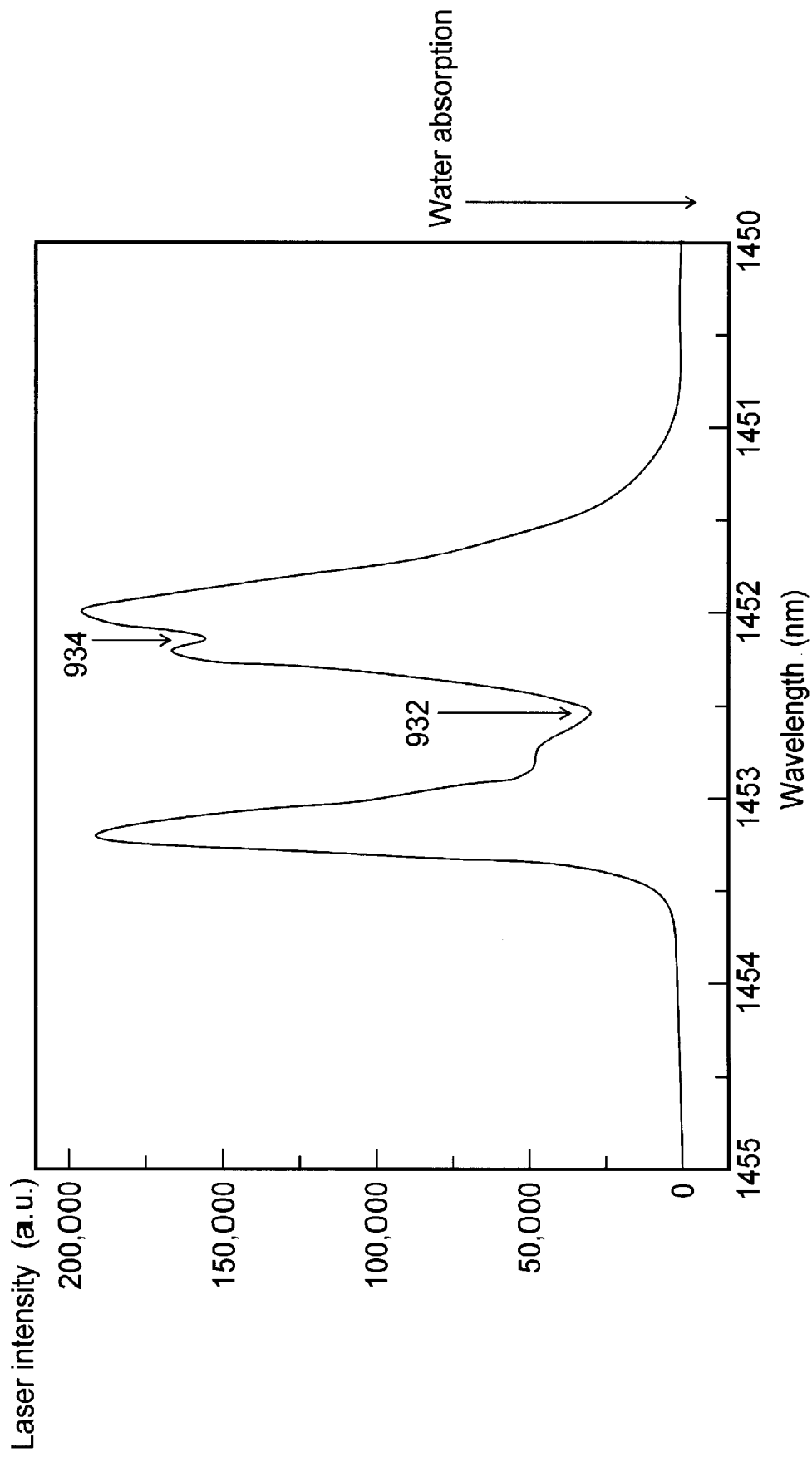
FIG. 5, on coordinates of laser intensity (in arbitrary units) and wavelength (in nanometers), is a graph showing an exemplary water absorption spectrum over the wavelengths of 1450 to 1455 nanometers.

In accordance with an aspect of the present invention, absorption data for water vapor recorded by the gas detection system 10 of the present invention is presented in FIG. 5. The spectral signature for water was obtained using an ILS laser 500 comprising an ion-doped crystal 507 made of $Tm^{+3}$, $Tb^{+3}$:YLF which was optically excited with a semiconductor diode laser 914. The gas detection system 10 employed to obtain the absorption data was similar to that shown schematically in FIG. 4 except that a modulator 926 was not employed. Rather, the electrical power to the semiconductor diode laser 914 was modulated instead. FIG. 5 shows a plot corresponding to the spectral signature of water for the spectral region between 1450 to 1455 nanometers in wavelength. Water absorption lines at 1452.5 and 1452.1 nanometers are indicated by arrows 934 and 936, respectively.

It will be appreciated that the output from the ILS laser 500 (beam G) can alternatively be transmitted via an optical fiber link to a remote site for spectral analysis. In particular, beam G can be coupled into an optical fiber or an optical fiber bundle. The output of the ILS laser 500, after having passed through the gaseous species, is thereby carried to the spectrometer assembly 600, which is located at the remote site. Under the proper conditions, it has been demonstrated that such optical fiber transmission does not distort the spectral data.

Table 2 summarizes a variety of configurations of the gas detection system 10 of the present invention. Each configuration corresponds to a separate embodiment of the present invention. The design parameters, which can be varied, that are listed in Table 2 include the following:

(1) The modulation may comprise a chopper, a pulser, or modulator external to the pumping source or modulation of the electric power to e.g., a semiconductor diode laser 914, which serves as the pumping source;

(2) The gas sample may be confined to a separate sample system 400A or may be confined to the chamber (or housing) 400;

(3) The output from the ILS laser 500 can be transmitted directly to the spectrometer assembly 600 or can be coupled into an optical fiber and carried to the spectrometer assembly; and (4) The spectral signature of the gaseous species can be obtained by using a fixed wavelength spectrometer and a multichannel detector 701 or by using a scanned wavelength spectrometer and a single channel detector.

nent that modifies the wavelength region over which the ILS laser 500 can potentially output light. This tuning element 944 is selected such that the wavelength range of the actual output of the ILS laser 500 overlaps the spectral absorption region of the gaseous species to be detected. Examples of wavelength selective optical elements 944 include a high-reflectance Fabry-Perot etalon (such as a metallized pellicle) that provides narrowband tuning, an optical bandpass filter, a diffraction grating, a prism, an electro-optical bandpass

TABLE 2

SUMMARY OF VARIOUS CONFIGURATIONS OF THE GAS DETECTION SYSTEM OF THE PRESENT INVENTION

| Modulation | Sample Cell | Optical Connection | Spectrometer/Detector |
|---|---|---|---|
| None | (1) Intracavity cell with sealed windows OR (2) Housing only | (1) Direct or use mirrors to direct beam OR (2) Fiber-optic coupler | (1) Fixed wavelength spectrometer and multichannel detector OR (2) Scanned wavelength spectrometer and single channel detector |
| Chopper, pulser, or modulator (located between pumping source and ILS laser) | (1) Intracavity cell with sealed windows OR (2) Housing only | (1) Direct or use mirrors to direct beam OR (2) Fiber-optic coupler | (1) Fixed wavelength spectrometer and multichannel detector OR (2) Scanned wavelength spectrometer and single channel detector |
| Electronic modulation of diode laser power above and below threshold | (1) Intracavity cell with sealed windows OR (2) Housing only | (1) Direct or use mirrors to direct beam OR (2) Fiber-optic coupler | (1) Fixed wavelength spectrometer and multichannel detector OR (2) Scanned wavelength spectrometer and single channel detector |

Additionally, a modulator 304 may control the transmission of the output of the ILS laser 500 to the spectrometer assembly 600 and the detector assembly 700 or the detector may be switched on and off rather than employing modulator 304. Alternatively, the detector assembly 700 may be continuously activated without the use of modulator 304 by pulsing the output of the pumping source 100, e.g., semiconductor diode laser 914.

Figure 6:
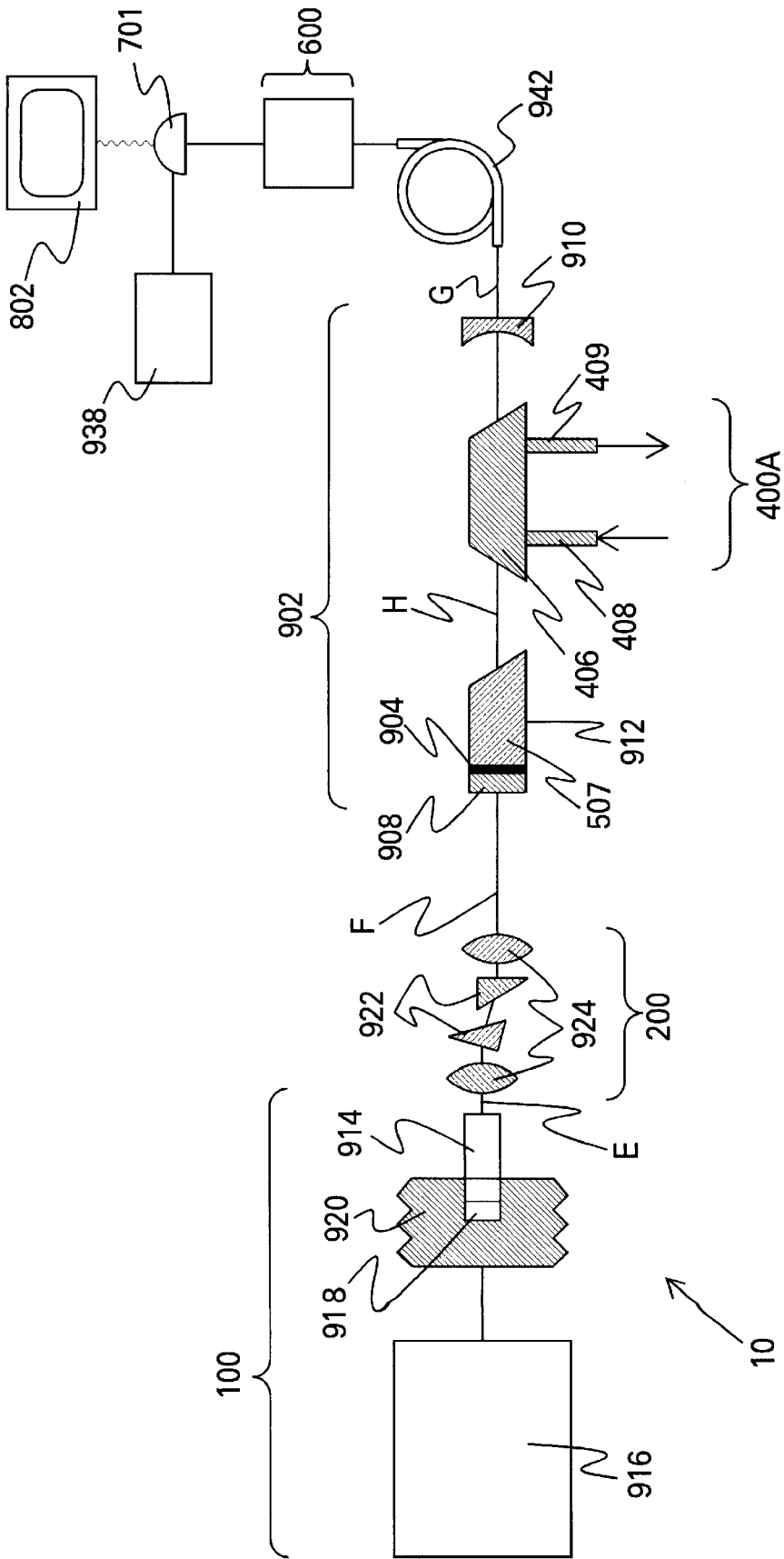
FIG. 6 is a schematic representation of an alternative embodiment of the ILS laser of the present invention wherein the laser light emanating from the laser cavity is coupled to the spectrometer assembly via a fiber optic link.

FIG. 6 shows an embodiment of the ILS laser 500 of the present invention that includes means (circuitry) 938 for periodically switching the detector 701 on and off, as well as means (circuitry) 940 for varying electrical power supplied to the diode laser 914. FIG. 6 also shows how output beam G can be carried to the spectrometer assembly 600 using a fiber optic link 942.

An additional embodiment of the ILS laser 500 of the present invention is shown in FIGS. 7A and 7B. As discussed above, the laser crystal 507 in an ILS laser 500 can be optically pumped using either longitudinal or transverse pumping. An example of transverse pumping is presented in FIGS. 7A and 7B, which depict an ILS laser 500 comprising an ion-doped crystal 507 that is pumped transversely using diode laser pumping. In particular, the ion-doped crystal 507 is pumped by a pump beam that is incident on a side 912 of the ion-doped crystal 507 such that the pump beam is directed perpendicular to the length, L, of the ion-doped crystal. In accordance with the present invention, optical pumping is provided by a semiconductor diode laser 914, or as depicted in FIGS. 7A and 7B, a semiconductor diode laser bar comprising a plurality of individual semiconductor diode lasers. Beam shaping optics 200 comprising a cylindrical lens are employed to couple the beam emanating from the semiconductor laser diode bar 914 to the ion-doped crystal 907.

The ILS laser 500 that is depicted in FIGS. 7A and 7B also includes a wavelength selective optical element 944 that tunes the ILS laser. The wavelength selective optical element (or tuning element) 944 is a separate optical compofilter, and combinations thereof. In the case where the high-reflectance Fabry-Perot etalon comprises a metallized pellicle, the pellicle may be tilted such that the optical beam is incident on a surface of the metallized pellicle that is not perpendicular the direction of propagation of the optical beam.

Figure 8:
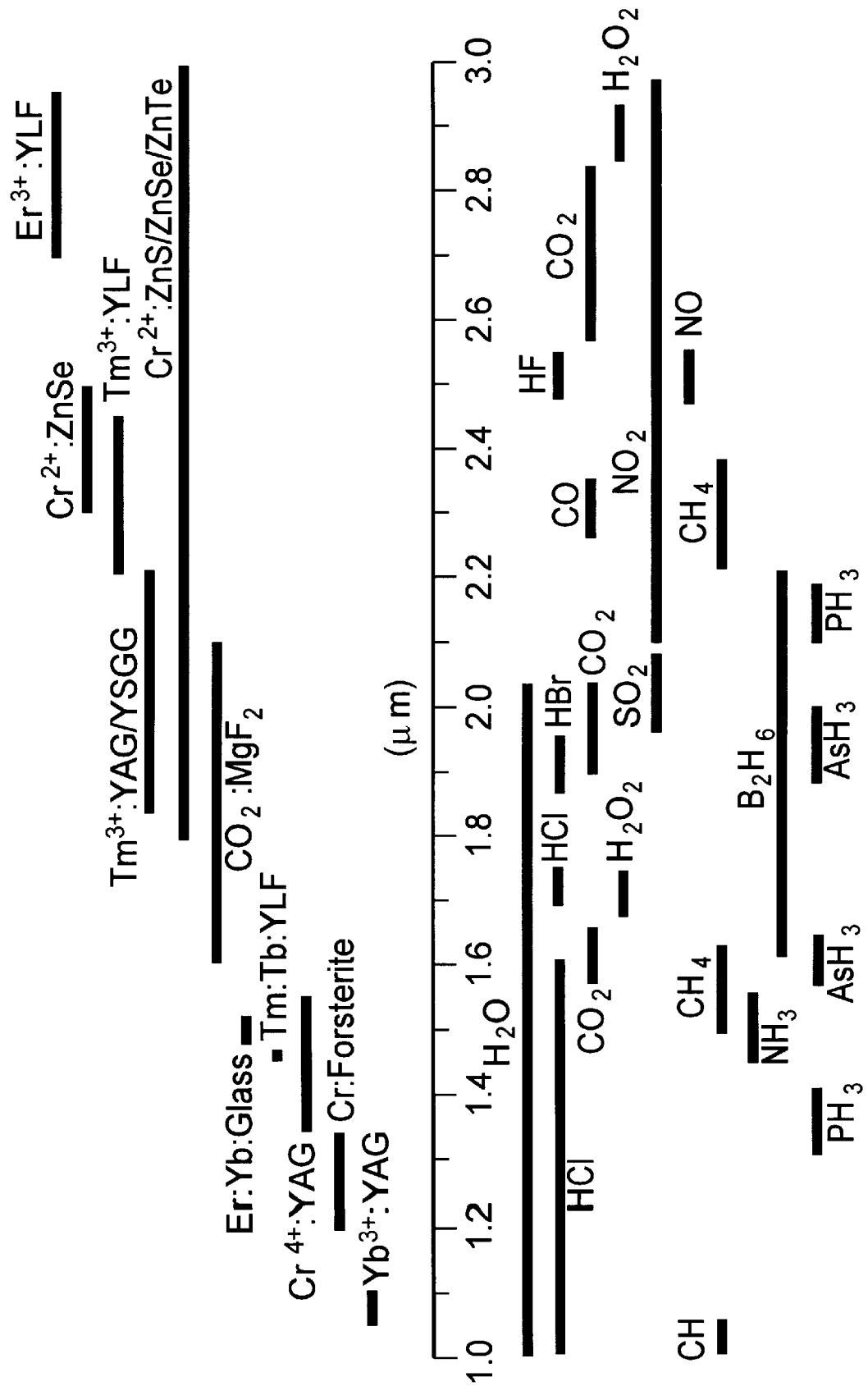
FIG. 8 is a listing of some ion-doped crystals that can be excited using a semiconductor diode laser and their respective tuning range as well as the near infrared spectral absorption regions of some gaseous species in the range of 1 to 3 micrometers in wavelength.

Advantageously, diode laser pumping can be employed to provide optical excitation for a variety of different types of ion-doped crystals 507, each having different compositions; see, e.g., Table 1. Consequently, the gas detection system 10 of the present invention can be used to detect a broad variety of gaseous species (i.e., molecules, atoms, radicals, and/or ions) having absorption features at widely varying wavelengths. FIG. 8 lists a limited number of ion-doped crystals 507 which are presently available that can be optically excited using a semiconductor diode laser 914 and their respective tuning ranges which reside in the wavelength range between about 1000 to 3000 nanometers. Ion-doped crystals 507 listed that operate as lasers in continuous (CW) mode at room temperature include the following: $Yb^{3+}$:YAG, Cr:Forsterite, $Cr^{4+}$:YAG, Tm:Tb:YLF, Er:Yb:Glass, $Tm^{3+}$: YAG/YSGG, $Tm^{3+}$:YLF, and $Er^{3+}$:YLF. Additionally, an ion-doped crystal 507 comprising $CO_2$:$MgF_2$ can operate in continuous mode when cryogenically cooled while an ion-doped crystal comprising $Cr^{2+}$:ZnSe can operate at room temperature in pulsed mode. (It will be appreciated that the potential tuning range of $Cr^{2+}$:ZnS/ZnSe/ZnTe is shown in FIG. 8.) FIG. 8 additionally shows the near infrared spectral absorption of some gaseous species. (It will be appreciated that the ranges in wavelength of the spectral absorption for $H_2O_2$, CO, $SO_2$, $CH_4$, and NO are calculated overtones.) Accordingly, FIG. 8 indicates some examples of the gaseous species that can be probed using an ILS laser 500 comprising an ion-doped crystal 507 which is optically pumped with a semiconductor laser diode 914.

In accordance with a preferred aspect of the present invention, the semiconductor diode laser 914, which may be employed as the source of optical pumping, is operated electrically. Consequently, the diode laser pumping source 100 is relatively small and compact in comparison to other sources of optical pumping. Additionally, given the low optical pumping energies required for diode laser pumping, the thermal management of the ILS laser 500 is less difficult than for gas detection systems 10 shown in prior art. Also, the cost is reduced and the operation is simplified in contrast to many gas detection systems 10 shown in prior art.

One limitation of the present invention observed by the inventors is that the spectrally resolved output of an ILS laser 500 having a linear laser cavity 902 may possess periodic structure that masks absorption features present in the output spectrum. A graph showing such periodic structure in the carbon dioxide ($CO_2$) absorption spectrum over the wavelengths of 2.014 to 2.021 micrometers is presented in FIG. 9. The carbon dioxide absorption spectrum displayed in FIG. 9 was obtained using an ILS laser 500 similar to the one shown in FIG. 4 except that modulator 926 was not employed. In particular, the ILS laser 500 used to obtain the spectrum depicted in FIG. 9 comprised a linear cavity 902 formed between first and second mirrors 908 and 910 wherein the first mirror comprised metallization deposited on one end 904 of the ion-doped laser crystal 507.

Figure 9:
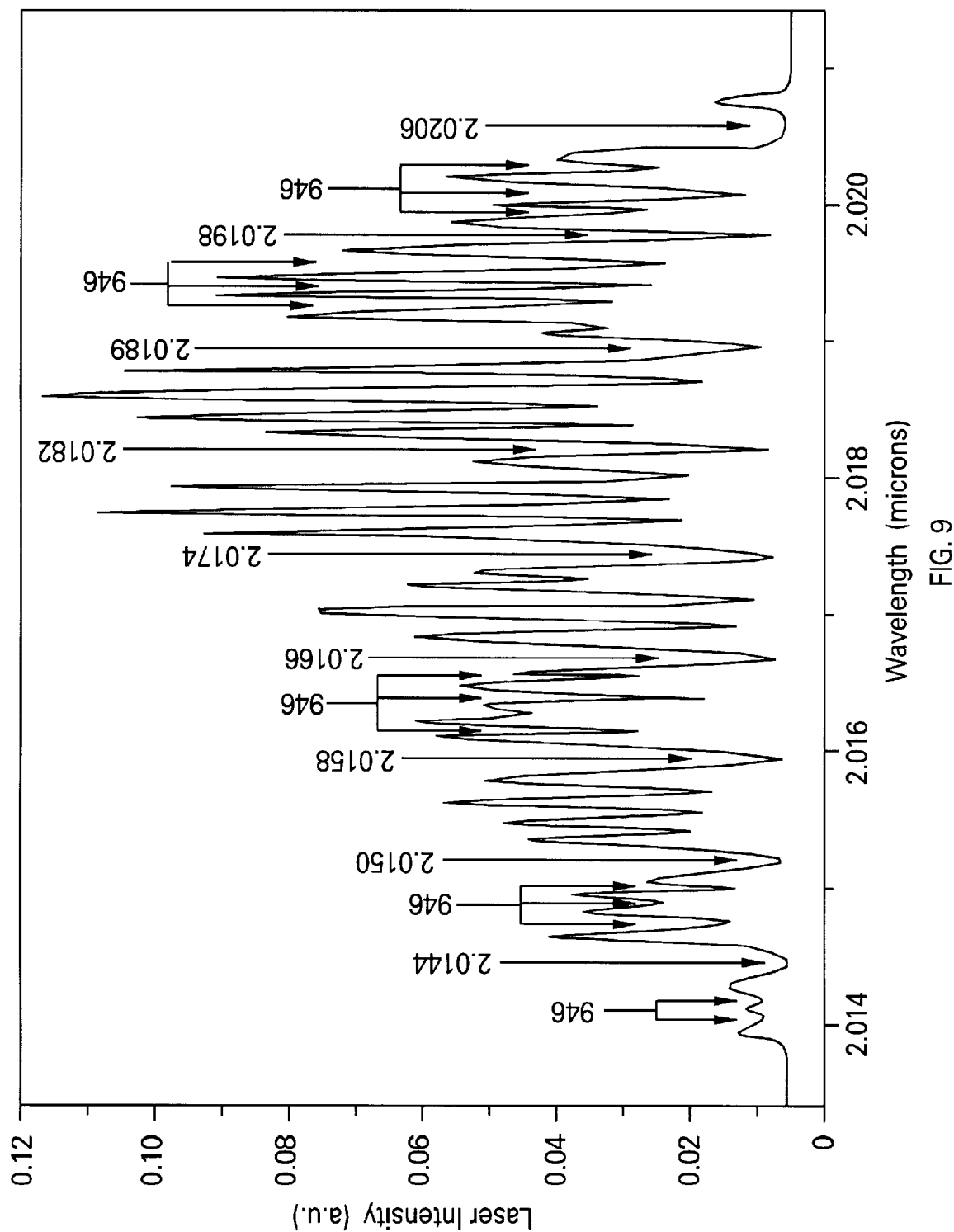
FIG. 9, on coordinates of laser intensity (in arbitrary units) and wavelength (in nanometers), is a graph showing periodic structure in the carbon dioxide ($CO_2$) absorption spectrum over the wavelengths of 2.014 to 2.021 micrometers that was obtained using a linear cavity formed between first and second mirrors wherein the first mirror comprises a high reflection coating deposited on one end of the ion-doped laser crystal.

Arrows 946 indicate some of the periodic structure in the absorption spectrum. The period of this structure that is shown in FIG. 9 is about 0.27 nanometers. Absorption lines at 2.0144, 2.0150, 2.0158, 2.0166, 2.0174, 2.0182, 2.0189, 2.0198, and 2.0206 micrometers are also indicated by arrows. It will be appreciated that if the period of the periodic structure is comparable to the width of an absorption line in the absorption spectrum, the periodic structure may hamper the detection of the absorption line.

Figure 10:
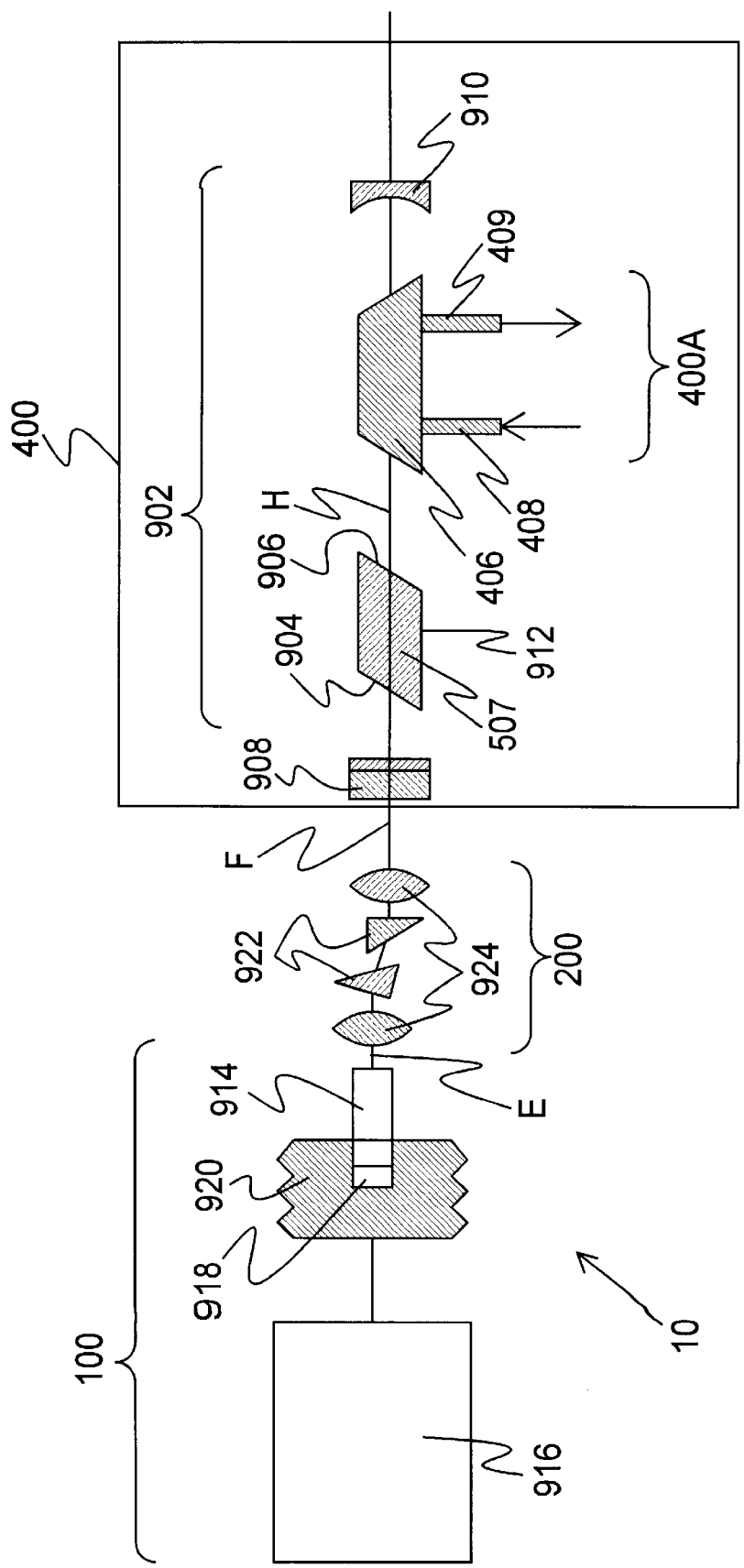
FIG. 10 is a schematic representation of an alternative embodiment of the ILS laser of the present invention wherein the linear laser cavity is formed between two mirrors that are separated from the ion-doped crystal laser medium and both ends of the ion-doped crystal are cut at angles not normal to the propagation direction of the beam within the laser cavity.

In accordance with a preferred embodiment of the present invention, this periodic structure can be minimized by forming the linear laser cavity 902 using two mirrors (908 and 910) that are separated from the ion-doped crystal laser medium 507. FIG. 10 shows a schematic representation of such an ILS laser 500 wherein the linear laser cavity 902 is formed between two mirrors 908 and 910 that are separated from the ion-doped crystal laser medium 507.

FIG. 10 also shows both ends 904 and 906 of the ion-doped crystal 507 cut at angles not normal to the propagation direction of the beam H within the laser cavity 902. The non-normal cut of the ends 904 and 906 prevents reflections from those ends from interfering with other reflections or wavefronts in the ILS laser 500 and creating a resultant interference and spatial hole burning effect that may show up in the spectral output of the laser. Preferably both ends 904 and 906 of the ion-doped crystal 507 are cut at Brewster's angle to minimize the amount of light reflected from the ends and, thus, reduce the loss in the laser cavity 902.

One possible explanation for the periodic structure in the spectral output of the ILS laser 500 is that spatial hole burning in the ion-doped crystal 507 supports a laser mode that fits exactly within the length of the crystal, which is 4 millimeters. It will be appreciated that a region having a length of 4 millimeters correlates to a free spectral range of 0.27 nanometers. The fact that the period of the structure within the spectral output of the ILS laser 500 is also 0.27 nanometers suggests that a laser mode that fits exactly within the 4 millimeter length of the ion-doped crystal 507 is responsible for this periodic structure.

In an ILS laser 500 where the first mirror 908 corresponds to one end 904 of the ion-doped crystal 507, a mode that fits in the ion-doped crystal and a mode that fits in the laser cavity 902 will be superimposed, thereby, increasing the likelihood that a laser mode that fits in both the ion-doped crystal and in the laser cavity 902 will be supported in the laser 500. Conversely, separating the first mirror 908 from the one end 904 of the ion-doped crystal 507 may reduce the likelihood that a laser mode that fits exactly within the length of the ion-doped crystal and within the length of the laser cavity 902 will be supported.

Figure 11:
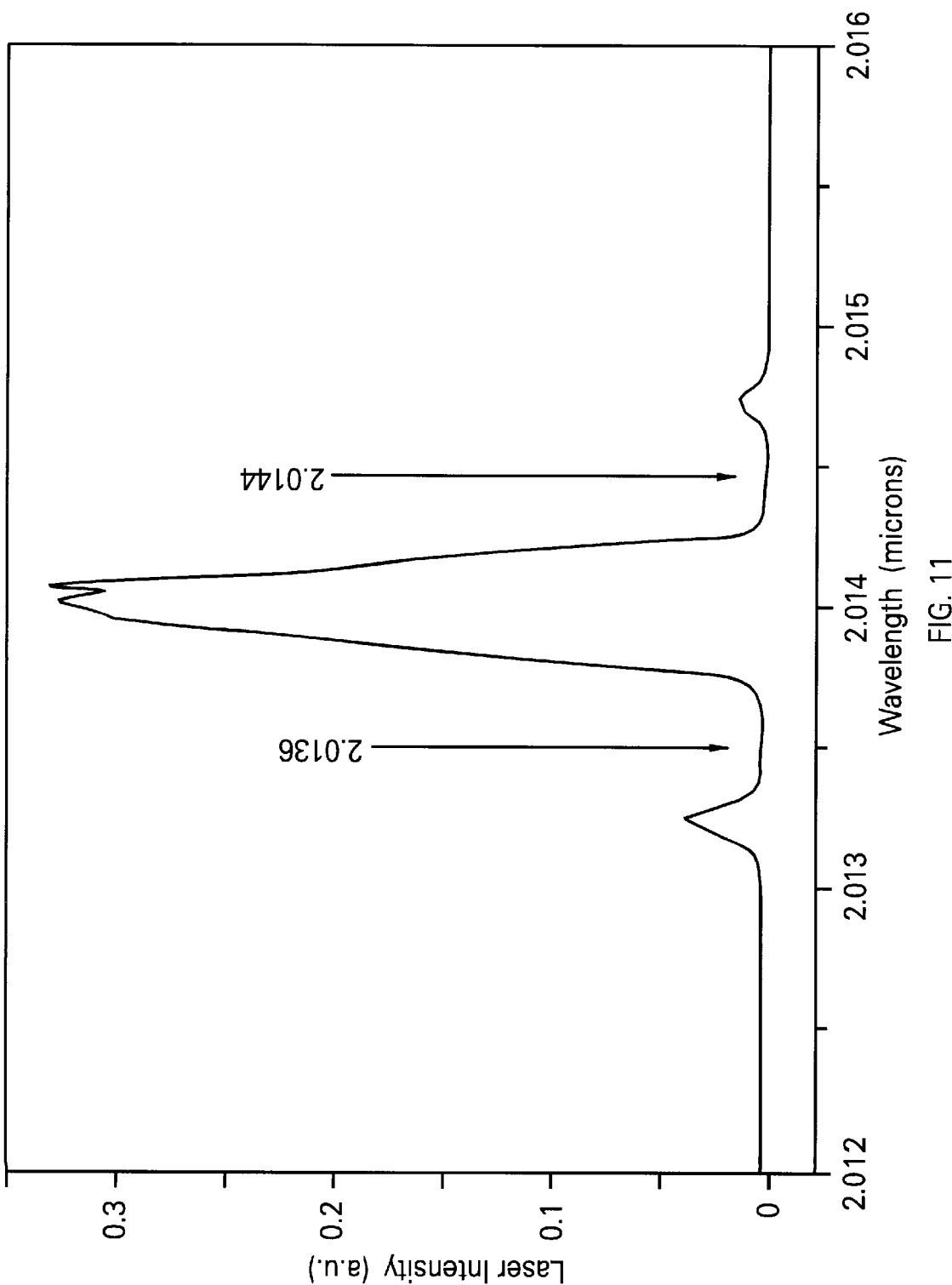
FIG. 11, on coordinates of laser intensity (in arbitrary units) and wavelength (in nanometers), is a graph showing the carbon dioxide, $CO_2$, absorption spectrum over the wavelengths of 2.013 to 2.015 micrometers that was obtained using a linear cavity formed between first and second mirrors that were separate from the ion-doped laser crystal.

The results of separating the mirrors 908 and 910 from the ion-doped laser crystal 507 are shown in FIG. 11. In particular, FIG. 11, shows a carbon dioxide ($CO_2$) absorption spectrum over the wavelengths of 2.013 to 2.015 micrometers that was obtained using an ILS laser 500 similar to that depicted in FIG. 10. Arrows at 2.0136 and 2.0144 micrometers indicate $CO_2$ absorption lines. It will be appreciated that the periodic structure is minimal over the wavelengths of about 2.0138 to 2.0143 micrometers of the carbon dioxide absorption spectrum displayed in FIG. 11. The results presented in FIG. 11 confirm the conclusion that separating the first mirror 908 from the one end 904 of the ion-doped crystal 507 minimizes the effects of the periodic structure described above. Accordingly, the design of the ILS laser 500 shown in FIG. 11 is advantageous.

More generally, the linear cavity design of the present invention offers many advantages over prior art gas detection systems 10. It will be appreciated that the linear laser cavity 902 of the present invention includes fewer optical elements than designs based on laser cavities defined by three mirrors. Accordingly, the complexity of the external cavity is reduced thereby increasing mechanical stability (i.e., ruggedness), as well as lowering the cost of the gas detection system 10.

The small/compact size of the gas detection system 10 based on the linear laser cavity 902 is amenable to a broad variety of practical applications. Specifically, the compactness of the gas detection system 10 comprising an ion-doped crystal 507 within a linear laser cavity 902 which has a semiconductor diode laser 914 as a pumping source 100 can be directed to a completely distinct set of applications in gas detection. In particular, the gas detection system 10 which utilizes a diode laser pump laser 100 for optical excitation of the ILS laser 500 is expected to find application in semiconductor manufacturing, process control, environmental monitoring, air quality and safety certification, health and safety certification, nuclear energy production, and medical diagnostics.

Thus, there has been disclosed an apparatus for detecting the presence and concentration of contaminants in a gas utilizing detector system 10. In accordance with a preferred embodiment of the present invention, a method for high sensitivity detection is also disclosed herein. The method suitably comprises reducing gases (contaminants) in sample chamber 400 to an acceptable level, placing a sample of gas to be detected in sample system 400A, pumping ILS laser 500 at or near threshold, periodically sampling the optical output from the ILS laser, preferably via modulation assembly 300 and modulator 304, measuring the absorption spectrum of the gases (contaminants) within the sample with spectrometer assembly 600 and detector assembly 700, and analyzing the absorption spectrum to identify the gaseous species (contaminants) and determine its concentration within the sample utilizing computer/software system 800. More particularly, reducing gases (contaminants) in chamber 400 (excluding sample system 400A) to an acceptable level may suitably comprise purging or evacuating the chamber such that the level of gases (contaminants) is below that to be detected in the gas sample within the sample system. As discussed previously, other mechanisms for reducing the level of gases (contaminants) may be utilized provided they can reduce the level to an acceptable level. Desirably, chamber 400 is effectively sealed prior to delivery to a user in a relatively tamper-proof manner.

A sample is suitably communicated to system 400A by connecting a gas line to connectors 408, 409 and feeding the gas into the sample system (for example, when the sample comprises a corrosive gas), or into the chamber 400 itself (for example, when the sample comprises a non-corrosive gas).

Pumping ILS laser 500 at or near threshold, more particularly, comprises selecting the correct pumping source 100 power, focusing conditions at laser crystal 507 utilizing beam modification optics 200, and modulation conditions utilizing modulator system 300. The method for detecting gaseous species in accordance with the present invention further comprises driving ILS laser 500 at or slightly above threshold. In accordance with the present invention, pump laser 100 suitably pumps ILS laser 500. Where necessary, pumping beam E is suitably shaped by beam shaping assembly 200 to meet the optical requirements of ILS laser 500. Further, where gas detection system 10 is operated in a pulsed or chopped mode, as described above, modulation assembly, and in particular, modulator 926 periodically interrupts pump beam F thereby preventing beam F from reaching ILS laser 500. Beam F output from modulator 926 and beam shaping assembly 200 is suitably directed to ILS laser 500.

In accordance with this method, as beam F enters chamber 400 through window (not shown) disposed in the wall of the chamber, beam F is suitably directed to ILS laser 500. Beam F suitably pumps crystal 507 at or near threshold, and the output beam is suitably directed to the gas sample within system 400A. The exiting beam, containing the absorption data from the gas (contaminant) sample, then exits gas chamber 400 through another window (not shown) suitably disposed in a wall of the chamber.

ILS laser 500 may be operated in a pulsed mode or a chopped mode using modulator 304, which is suitably synchronized to modulator 926, and which periodically samples the output beam from the ILS laser and passes the sampled output thus obtained to spectrometer assembly 600 and detector assembly 700. Alternatively, the electrical power supplied to the pumping source 100 (for example, when a diode laser pump laser is employed) may be modulated and synchronized with modulator 304. Suitably, mirrors 930 and 932 direct sampled output beam G from ILS laser 500 to spectrometer assembly 600 and detector assembly 700. Alternatively, instead of using modulator 304, detector assembly 700 may be switched on and off to sample the output from ILS laser 500.

The method for detecting gaseous species in accordance with the present invention further comprises analyzing output beam G from the ILS laser 500. Preferably, spectrometer assembly 600 spectrally resolves and detector assembly 700 suitably captures beam G from ILS laser 500. Spectrometer assembly 600 suitably spectrally disperses beam G from ILS laser 500 through beam expanding assembly optics, i.e., lenses 603 and 605, diffraction gratings 607, 609 and focusing lens 611. Spectrally-resolved ILS absorption data exiting spectrometer assembly 600 is suitably displaced spatially to be detected by multichannel detector 701.

It will be appreciated that the gas detection system 10 can be utilized to obtain absorption spectra for contaminants, such as water vapor, in corrosive (e.g., HCl) or non-corrosive (e.g., $N_2$) over a variety of wavelength regions.

Given the relationship between intensity and concentration, once a characteristic signature of the contaminant gas, e.g., water vapor, is obtained, the concentration of the contaminant contained within the sample can be readily obtained. In accordance with the present invention, computer 802 can be suitably programmed to interpret the data and provide an output indicative of the presence and/or concentration of the contaminant contained within the sample.

In accordance with the apparatus and method of the present invention, the output signal (beam G) from the ILS laser 500 is detected and analyzed to identify the gaseous species (via its spectral signature) and to determine its concentration. Those skilled in the art will appreciate that the detection levels available through practice of the present invention generally exceed those which are obtainable through use of conventional devices. Moreover, gas detection system 10 can be used in-line and readily obtain, near real-time measurement of the presence and amount of the contaminant contained in a specific sample, thus, addressing the many disadvantages associated with the use of such conventional devices. In particular, the method of the present invention provides rapid, in situ detection of gaseous species within gas samples at detection levels which are not available in prior art.

It should be understood that the foregoing description relates to preferred exemplary embodiments of the invention, and that the invention is not limited to the specific forms shown herein. Various modifications may be made in the design and arrangement of the elements set forth herein without departing from the scope of the invention as expressed in the appended claims. Moreover, the application of gas detection system 10 as well as the location of the ILS gas detector, e.g., in a semiconductor fabrication assembly, can vary as may be desired. For example, the specific placement of the various elements within the ILS chamber 400 and gas detector system 10 itself may be modified so long as their configuration and placement suitably enables optical excitation of ILS laser 500 in a readily reproducible manner. These and other modifications in the design, arrangement, and application of the present invention as now known or hereafter devised by those skilled in the art are contemplated by the amended claims.

What is claimed is:

1. A gas detection system for detecting the presence of gaseous species in a gas sample comprising:

(a) a linear laser cavity formed between a first mirror and a second mirror;

(b) an ion-doped crystal therein having two ends;

(c) a pumping source located outside said linear laser cavity, which has an output that optically excites said ion-doped crystal, thereby producing an output beam that exits said linear laser cavity;

(d) beam shaping optics located outside said linear laser cavity that shapes said output of said pumping source, wherein said beam shaping optics are selected from the group consisting of diffractive optics, fiber optics, refractive optics, gradient index optics wherein the refractive index varies axially, gradient index optics wherein the refractive index varies radially, micro-optics, and combinations thereof;

(e) a container for containing said gas sample in said linear laser cavity, said output beam of said ion-doped crystal passing through said gas sample prior to exiting said linear laser cavity;

(f) a spectrometer wherein said output beam of said ion-doped crystal after exiting said linear laser cavity is directed to said spectrometer; and (g) a detector assembly including therein a detector, wherein said output beam of said ion-doped crystal after exiting said spectrometer is directed to said detector assembly for determining the presence and/or concentration of gaseous species in the gas sample.

2. The gas detection system of claim 1 wherein said pumping source is selected from the group consisting of a gas laser, a solid-state crystal laser, a semiconductor laser diode, and at least one flash pump.

3. The gas detection system of claim 1 wherein said ion-doped crystal is longitudinally pumped.

4. The gas detection system of claim 1 wherein said ion-doped crystal is transversely pumped.

5. The gas detection system of claim 1 wherein said first mirror comprises a reflective coating deposited on one end of said ion-doped laser crystal and said second mirror comprises a curved reflector and wherein said end of said ion-doped crystal that is closest to said second mirror is cut such that the normal to said end is at a non-zero angle with respect to the propagation direction of said output beam of said ion-doped crystal.

6. The gas detection system of claim 1 wherein said first mirror and said second mirror are separated from said ion-doped crystal.

7. The gas detection system of claim 6 wherein said end of said ion-doped crystal closest to said first mirror is cut such that the normal to said end is at a first non-zero angle with respect to the propagation direction of the output of said pumping source incident thereon.

8. The gas detection system of claim 7 wherein said end of said ion-doped crystal that is closest to said second mirror is cut such that the normal to said end is at a second non-zero angle with respect to the propagation direction of said output beam of said ion-doped crystal.

9. The gas detection system of claim 8 wherein said first and second non-zero angles correspond to Brewster's angle.

10. The gas detection system of claim 1 wherein said spectrometer and said detector respectively comprise either (a) a spectrometer fixed in wavelength and a multichannel detector or (b) a spectrometer scanned in wavelength and a single channel detector.

11. The gas detection system of claim 1 wherein said linear laser cavity is contained within a chamber configured for removal of said gaseous species to be detected.

12. The gas detection system of claim 11 wherein said gas sample is contained within said chamber.

13. The gas detection system of claim 12 wherein said gas sample is contained within a sample cell contained within said chamber.

14. The gas detection system of claim 1 wherein said output beam of said ion-doped crystal is alternately switched on and off.

15. The gas detection system of claim 14 wherein said output of said pumping source is periodically switched between intensity levels thereby causing said output beam of said ion-doped crystal to be alternately switched on and off.

16. The gas detection system of claim 15 wherein said output of said pumping source is periodically switched using either a modulation assembly or circuitry for varying electrical power supplied to said pumping source.

17. The gas detection system of claim 16 wherein said modulation assembly has an effect on the output of said pumping source that is selected from the group consisting of chopping, pulsing that causes said output of said pumping source to alternate between zero intensity and a non-zero intensity value over a duty cycle that may be varied, and modulating that causes said output of said pumping source to fluctuate alternately between two non-zero intensity levels to bring said ILS laser alternately above and below threshold.

18. The gas detection system of claim 1 wherein said output beam that exits said linear laser cavity is alternately prevented from reaching said detector assembly.

19. The gas detection system of claim 1 wherein said detector is periodically switched on and off.

20. The gas detection system of claim 1 wherein said beam shaping optics are selected from the group consisting of (i) anamorphic prisms and lenses and (ii) a beam expanding telescope.

21. The gas detection system of claim 1 wherein said ion-doped crystal comprises a material selected from the group consisting of Cr:Tm:Ho:YAG, $Cr^{4+}$:YSO, $Cr^{4+}$:YAG, $Cr^{4+}$:YSAG, Er:GSGG, $Er^{3+}$:YLF, $Er^{3+}$:$Yb^{3+}$:glass, $Ho^{3+}$:YSGG, $Ho^{3+}$:$Tm^{3+}$:LUAG, $Tm^{3+}$:$Ho^{3+}$:YLF, $Tm^{3+}$:$Ho^{3+}$:YAG, $Tm^{3+}$:Ca Y SOAP, $Tm^{3+}$:YLF, $Tm^{3+}$:$Tb^{3+}$:YLF, $Tm^{3+}$:glass, $Tm^{3+}$:Ca La SOAP, $Tm^{3+}$:YOS, $Tm^{3+}$:YSGG, $Tm^{3+}$:YAG, $Yb^{3+}$:YAG, Cr:Forsterite, Er:Yb:Glass, $CO_2$:$MgF_2$, $Cr^{2+}$:ZnSe, $Ti^{3+}$:$Al_2O_3$, $Ni^{2+}$:$BaLiF_3$, $Tm^{3+}$: $YVO_4$, $Nd^{3+}$: $YVO_4$, $Nd^{3+}$:YLF, and $Nd^{3+}$:YAG, and $Cr^{2+}$:ZnS/ZnSe/ZnTe.

22. A method for detecting the presence of gaseous species in a gas sample, comprising the steps of:

(a) providing a linear laser cavity formed between a first mirror and a second mirror having an ion-doped crystal contained therein;

(b) providing a pumping source situated so that the output beam of said pumping source is directed to said ion-doped crystal to thereby pump said crystal to produce an output beam from said ion-doped crystal;

(c) providing a container for containing said gas sample in said linear laser cavity so that said output beam from said ion-doped crystal passes through said gas sample prior to exiting said linear laser cavity;

(d) providing beam shaping optics outside said linear laser cavity that shape said output of said pumping source, said beam shaping optics being selected from the group consisting of diffractive optics, refractive optics, fiber optics, gradient index optics wherein the refractive index varies axially, gradient index optics wherein the refractive index varies radially, micro-optics, and combinations thereof;

(e) providing a spectrometer situated so that said output beam from said ion-doped crystal after exiting said linear laser cavity is directed to said spectrometer; and (f) providing a detector assembly situated so that said output beam from said ion-doped crystal after exiting said spectrometer is directed to said detector assembly for determining the presence and/or concentration of gaseous species in said gas sample.

23. The method of claim 22 wherein said pumping source is selected from the group consisting of a gas laser, a solid-state crystal laser, a semiconductor laser diode, and at least one flash pump.

24. The method of claim 22 wherein said ion-doped crystal is longitudinally pumped.

25. The method of claim 22 wherein said ion-doped crystal is transversely pumped.

26. The method of claim 22 wherein said first mirror and said second mirror are separated from said ion-doped crystal.

27. The method of claim 26 wherein said end of said ion-doped crystal closest to said first mirror is cut such that the normal to said end is at a first non-zero angle with respect to the propagation direction of the output of said pumping source incident thereon.

28. The method of claim 27 wherein said end of said ion-doped crystal that is closest to said second mirror is cut such that the normal to said end is at a second non-zero angle with respect to the propagation direction of said output beam of said ion-doped crystal.

29. The method of claim 28 wherein said first and second non-zero angles correspond to Brewster's angle.

30. The method of claim 22 wherein said spectrometer and said detector assembly respectively comprise either (a) a spectrometer fixed in wavelength and a multichannel detector or (b) a spectrometer scanned in wavelength and a single channel detector.

31. The method of claim 22 wherein said linear laser cavity is contained within a chamber configured for removal of said gaseous species to be detected.

32. The method of claim 31 wherein said gas sample is contained within said chamber.

33. The method of claim 31 wherein said gas sample is contained within a sample cell contained within said chamber.

34. The method of claim 22 wherein said output beam of said ion-doped crystal is alternately switched on and off.

35. The method of claim 34 wherein said output of said pumping source is periodically switched between intensity levels thereby causing said output beam of said ion-doped crystal to be alternately switched on and off.

36. The method of claim 35 wherein periodically switching said output of said pumping source is achieved by a method selected from the group consisting of chopping, pulsing that causes said output of said pumping source to alternate between zero intensity and a non-zero intensity value over a duty cycle that may be varied, modulating that causes said output of said pumping source to fluctuate alternately between two non-zero intensity levels to bring said ion-doped crystal alternately above and below threshold, and varying electrical power supplied to said pumping source.

37. The method of claim 22 wherein said output beam that exits said linear laser cavity is alternately prevented from reaching said detector assembly.

38. The method of claim 22 wherein said detector assembly includes therein a detector that is periodically switched on and off.

39. The method of claim 22 wherein said beam shaping optics are selected from the group consisting of (i) anamorphic prisms and lenses and (ii) a beam expanding telescope.

40. The method of claim 22 wherein said ion-doped crystal comprises a material selected from the group consisting of Cr:Tm:Ho:YAG, $Cr^{4+}$:YSO, $Cr^{4+}$:YAG, $Cr^{4+}$:YSAG, Er:GSGG, $Er^{3+}$:YLF, $Er^{3+}$:$Yb^{3+}$:glass, $Ho^{3+}$:YSGG, $Ho^{3+}$:$Tm^{3+}$:LUAG, $Tm^{3+}$:$Ho^{3+}$:YLF, $Tm^{3+}$:$Ho^{3+}$:YAG, $Tm^{3+}$:Ca Y SOAP, $Tm^{3+}$:YLF, $Tm^{3+}$:$Tb^{3+}$:YLF, $Tm^{3+}$:glass, $Tm^{3+}$:Ca La SOAP, $Tm^{3+}$:YOS, $Tm^{3+}$:YSGG, $Tm^{3+}$:YAG, $Yb^{3+}$:YAG, Cr:Forsterite, Er:Yb:Glass, $CO_2$:$MgF_2$, $Cr^{2+}$:ZnSe, $Ti^{3+}$:$Al_2O_3$, $Ni^{2+}$:$BaLiF_3$, $Tm^{3+}$: $YVO_4$, $Nd^{3+}$:$YVO_4$, $Nd^{3+}$:YLF, $Nd^{3+}$:YAG, and $Cr^2+$:ZnS/ZnSe/ZnTe.

41. The method of claim 22 wherein said first mirror and said second mirror are the only mirrors used to form said linear laser cavity.

* * * * *